United States Patent
Forrest et al.

(10) Patent No.: US 9,062,368 B2
(45) Date of Patent: Jun. 23, 2015

(54) METHOD OF MONITORING PHOTOACTIVE ORGANIC MOLECULES IN-SITU DURING GAS-PHASE DEPOSITION OF THE PHOTOACTIVE ORGANIC MOLECULES

(71) Applicant: The Regents of the University of Michigan, Ann Arbor, MI (US)

(72) Inventors: Stephen R. Forrest, Ann Arbor, MI (US); Garen Vartanian, Ann Arbor, MI (US); Cedric Rolin, Lasne (BE)

(73) Assignee: The Regents of the University of Michigan, Ann Arbor, MI (US)

( * ) Notice: Subject to any disclaimer, the term of this patent is extended or adjusted under 35 U.S.C. 154(b) by 172 days.

(21) Appl. No.: 13/652,593

(22) Filed: Oct. 16, 2012

(65) Prior Publication Data

US 2014/0106062 A1     Apr. 17, 2014

(51) Int. Cl.
C23C 14/52 (2006.01)
C23C 14/12 (2006.01)
C23C 14/24 (2006.01)
C23C 14/54 (2006.01)
G01N 21/64 (2006.01)
G01N 21/84 (2006.01)

(52) U.S. Cl.
CPC ............... *C23C 14/12* (2013.01); *C23C 14/24* (2013.01); *C23C 14/52* (2013.01); *C23C 14/547* (2013.01); *G01N 21/64* (2013.01); *G01N 21/6489* (2013.01); *G01N 2021/8416* (2013.01)

(58) Field of Classification Search
CPC ............................ G01N 21/64; G01N 21/6489
See application file for complete search history.

(56) References Cited

U.S. PATENT DOCUMENTS

| | | | |
|---|---|---|---|
| 5,213,985 A | 5/1993 | Sandroff et al. | |
| 5,272,089 A | 12/1993 | Vo-Dinh | |
| 5,403,433 A | 4/1995 | Morrison et al. | |
| 5,525,520 A | 6/1996 | Dinh | |
| 5,695,556 A | 12/1997 | Tamamura et al. | |
| 7,424,389 B2 * | 9/2008 | Marcus et al. | 702/172 |
| 8,742,370 B2 * | 6/2014 | Tkachuk | 250/458.1 |
| 2007/0298159 A1 * | 12/2007 | Bender et al. | 427/8 |
| 2012/0258239 A1 * | 10/2012 | Hoffmann | 427/10 |
| 2013/0209666 A1 * | 8/2013 | Kamada et al. | 427/8 |

FOREIGN PATENT DOCUMENTS

| | | | |
|---|---|---|---|
| JP | 2008169457 A | * | 7/2008 |
| WO | WO2012026483 A1 | * | 3/2012 |

OTHER PUBLICATIONS

Sawtell et al. 2D Species Concentration Mapping of Thermal AP-CVD Reactors for Monitoring, Control and Design. ECS Transaction, 25 (8), pp. 501-506, 2009.*

(Continued)

Primary Examiner — David Turocy
(74) Attorney, Agent, or Firm — Duane Morris LLP

(57) ABSTRACT

A method for in-situ monitoring of gas-phase photoactive organic molecules in real time while depositing a film of the photoactive organic molecules on a substrate in a processing chamber for depositing the film includes irradiating the gas-phase photoactive organic molecules in the processing chamber with a radiation from a radiation source in-situ while depositing the film of the one or more organic materials and measuring the intensity of the resulting photoluminescence emission from the organic material. One or more processing parameters associated with the deposition process can be determined from the photoluminescence intensity data in real time providing useful feedback on the deposition process.

10 Claims, 15 Drawing Sheets

(56) References Cited

OTHER PUBLICATIONS

Burns, Iain S. et al., Diode Laser Induced Florescence for Gas-Phase Diagnostics, Z. Phys. Chem., 225 (11-12). pp. 1343-1368.

Carstea, Elfrida M., Florescence Spectroscopy as a Potential Tool for In-Situ Monitoring of Dissolved Organic Matter in Surface Water Systems, an article in the book "Water Pollution", Published: Feb. 24, 2012, Publisher: InTech.

* cited by examiner

A. Aziz, K.L. Narasimhan, Synthetic Metals 122 (2001) 53-54

METHOD OF MONITORING PHOTOACTIVE ORGANIC MOLECULES IN-SITU DURING GAS-PHASE DEPOSITION OF THE PHOTOACTIVE ORGANIC MOLECULES

GOVERNMENT RIGHTS

This invention was made with government support under DE-SC0005310 awarded by the U.S. Department of Energy. The government has certain rights in the invention.

JOINT RESEARCH AGREEMENT

The claimed invention was made by, on behalf of, and/or in connection with one or more of the following parties to a joint university corporation research agreement: The Regents of the University of Michigan, Princeton University, University of Southern California, Global Photonic Energy Corporation, and Universal Display Corporation. The agreement(s) was in effect on and before the date the claimed invention was made, and the claimed invention was made as a result of activities undertaken within the scope of the agreement(s).

TECHNICAL FIELD

The present disclosure relates to the field of organic optoelectronics and particularly to deposition of photoactive organic films for use in optoelectronics. More particularly, the present disclosure relates to monitoring photoactive organic molecules in-situ during gas-phase deposition of the photoactive organic molecules as a thin film.

BACKGROUND

Organic electronic and optoelectronic devices such as photovoltaic (PV) devices require deposition of at least one functional film of organic molecules. The organic films can be grown on a substrate through many techniques, for example, vacuum thermal evaporation (VTE), organic vapor phase deposition (OVPD), chemical vapor deposition (CVD), etc. In a VTE process, a powder of organic species is thermally evaporated within a vacuum chamber and a fraction of the evaporated molecules condense on the substrate. In an OVPD process, an organic powder is also evaporated, but in a stream of hot inert carrier gas that transports the organic molecules to a substrate on which the evaporated organic molecules condense.

These techniques for deposition of organic films require a way to reproducibly control growth rate and thin film thickness in real time and in-situ. In the event of a co-deposition of two or more organic species, a system to precisely monitor and control material mixing is also desirable.

Quartz crystal monitoring (QCM) has been generally used to monitor the mass of material deposited on the substrate by measuring the mass of material deposited on the surface of a quartz crystal placed in a close proximity to the substrate. In a VTE process, a precise reading of the deposited mass by QCM can be achieved by means of frequent replacement and recalibration. However, the control over co-deposition of at least two organic molecules in a VTE process requires the use of several QCMs in parallel, and the control remains tedious and imprecise. In an OVPD process, the use of QCM is more delicate and impractical because the frequency shift of a quartz crystal, which is necessary for signal generation, depends not only on the mass deposited but also on temperature and viscosity of the surrounding medium. Therefore, a better technique for monitoring photoactive organic film deposition processing parameters is highly desirable, particularly in an OVPD process.

SUMMARY

The present disclosure provides a method for in-situ monitoring of photoactive organic molecules in real time while depositing a film of one or more photoactive organic materials from a gas-phase state onto a substrate in a processing chamber. According to one embodiment, the method comprises (a) irradiating at least one of the one or more gas-phase organic materials in the processing chamber with a radiation beam in-situ while the one or more organic materials is being deposited on the substrate as a film, thereby generating a photoluminescence (PL) emission from each of the irradiated gas-phase organic materials. As the PL emission is being generated, (b) the intensity of the PL emission from each of the irradiated gas-phase organic materials is measured using a detector. From each of the measured PL emission intensity values, (c) at least one processing parameter associated with depositing the one or more gas-phase photoactive organic materials is determined. According to an embodiment, the measured intensity data of the photoluminescence emission from the at least one of the one or more gas-phase photoactive organic materials can be stored during the deposition process and step (c) is carried out at a later time. In another embodiment, the step (c) can be performed in real time while the film is being deposited. This ability to monitor at least one processing parameter in-situ and in real time during the deposition process provides a useful and valuable feedback information for controlling the deposition process.

The present method can be implemented in an OVPD process as well as a VTE process. The examples of the at least one processing parameters that can be determined in real time while depositing the film of the photoactive organic materials onto the substrate in the processing chamber include, but are not limited to, the concentration levels and the deposition rates of the one or more gas-phase photoactive organic materials in the processing chamber. Additionally, in an OVPD embodiment, the flow rate of the photoactive organic materials in the processing chamber can also be monitored using the one or more gas-phase organic materials as a tracer for the carrier gas.

In some embodiments, determining the at least one processing parameter is performed in a steady state of depositing the organic film in the processing chamber. In other embodiments, determining the at least one processing parameter is performed in a non-steady dynamic state of depositing the organic film in the processing chamber. The non-steady dynamic state may comprise a dynamic perturbation. In some embodiments, the method comprises responding to a dynamic perturbation by making adjustments to providing the at least one photoactive organic gas in the processing chamber.

The radiation beam is generated using at least one radiation source configured to emit radiation, such as laser light beam, having an appropriate wavelength that matches the absorption spectrum of the one or more gas-phase photoactive organic material being irradiated so that sufficient amount of PL emission is generated by the one or more gas-phase photoactive organic material. The detector for measuring the intensity of the PL emission can be an appropriate detector such as a photodetector or a spectrometer. As will be described in more detail below, the detector can comprise one or more photodetectors or one or more spectrometers. The detectors can be located inside, outside or on the wall of the processing chamber, In an embodiment where OVPD process is used for depositing the one or more organic material, a carrier gas is provided in the processing chamber, together with the one or more gas-phase organic materials.

Additionally, when a radiation source that can be directed and focused to a small region is used for probing/irradiating the one or more photoactive organic materials in the processing chamber, this provides a spatial resolution when measuring the concentration of the organic material in the processing chamber. A laser light beam is an example of such radiation source for irradiating the one or more photoactive organic materials in the processing chamber. This spatial resolution provides the ability to study the local distribution of the concentration levels of the organic materials in the processing chamber which allows the study of diffusion of the gas-phase organic materials across the boundary layer of the carrier gas on the substrate.

Accordingly, the present disclosure also discloses a method for generating a spatial concentration level distribution map of a gas-phase photoactive organic material in a processing chamber wherein the inside of the processing chamber is predefined into a plurality of zones, each of the plurality of zones having a location identifier. The method comprises irradiating one of the plurality of zones with a laser beam, thereby generating a photoluminescence emission from the gas-phase photoactive organic material in that particular zones. Next, the intensity of the PL emission in the one of the plurality of zones is measured and the concentration level of the gas-phase photoactive organic material in the zone is determined from the PL emission intensity data. By pairing the concentration level of the gas-phase photoactive organic material in the zone with the location identifier for the zone and repeating this process for each of the plurality of zones, a series of paired data of the concentration level of the gas-phase photoactive organic material and the location identifiers for the corresponding zones is generated. This series of paired data forms the spatial concentration level distribution map of the gas-phase photoactive organic material in the processing chamber.

The method of the present disclosure is applicable to a large array of materials and processing techniques and because it is not invasive the method has the ability to monitor in-situ, in real time without interrupting the deposition process.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like numerals denote like features throughout specification and the drawings.

DETAILED DESCRIPTION

Figure 1:
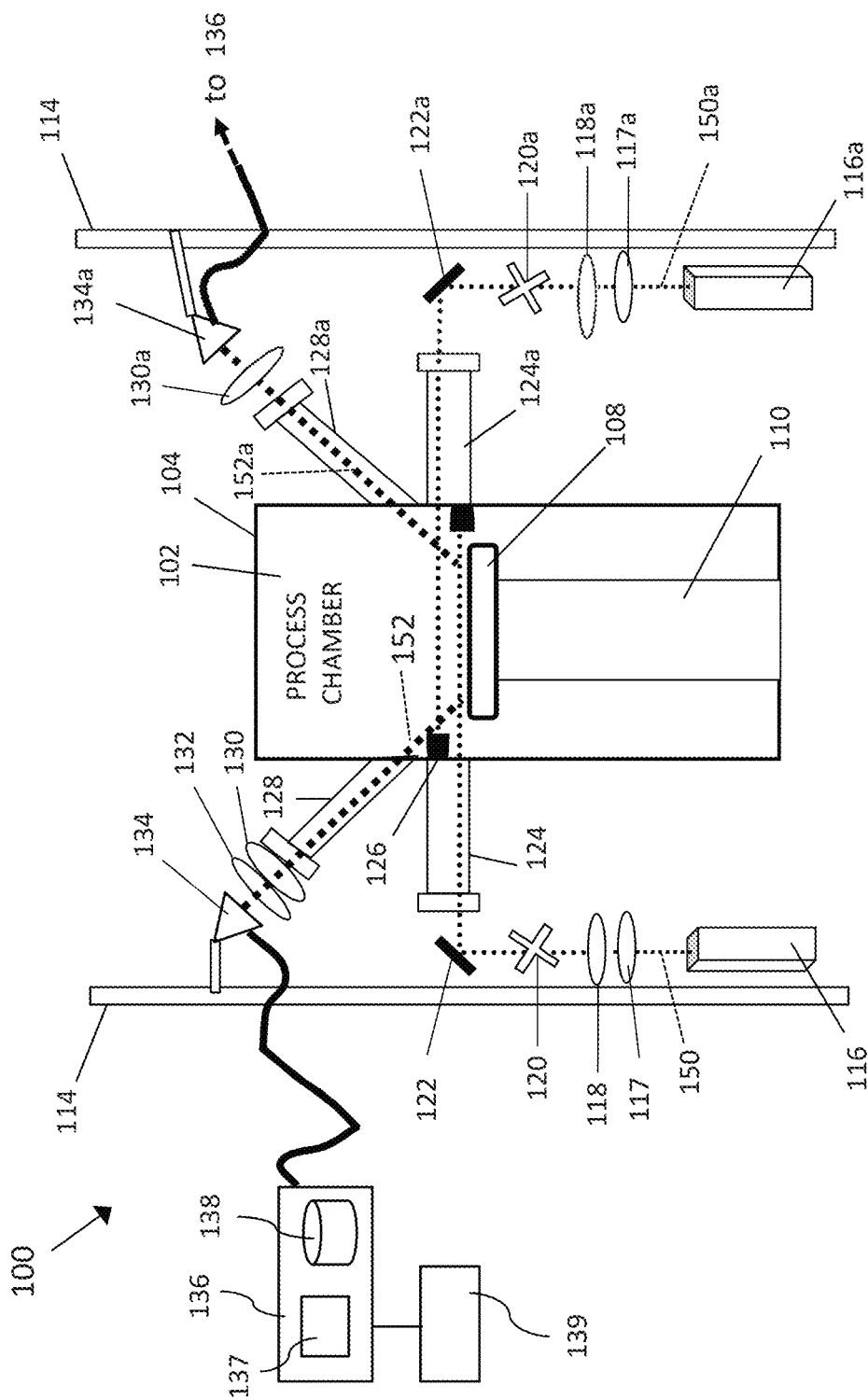
FIG. 1 is a schematic illustration of a deposition chamber configured for in-situ monitoring organic molecules through photoluminescence emission according to an embodiment.

Photoluminescence (PL) spectroscopy (including fluorescence and phosphorescence spectroscopy) is a characterization technique in which a beam of electromagnetic radiation, such as laser light, is used to probe and excite molecular or atomic species. The incident light is absorbed by the studied species, which results in a population of higher excited electronic and vibration states. Among different electronic relaxation pathways, some are radioactive, resulting in the PL emission (light) from the stimulated molecules. The PL emission is usually proportional to concentration of emitting species. The PL emission also indicates the nature of the molecular electronic and vibrational states. PL spectroscopy is usually applied either to a solution containing the species or to solid state samples, for example thin films of organic species. PL spectroscopy is less frequently used to study atoms and small molecules such as $NO_2$, $NO_3$, CH, and OH in a range of gas phase systems including flames, plasmas and the atmosphere. But gas-phase PL spectroscopy has not been applied to heavier organic species such as photoactive organic molecules, especially to gas-phase photoactive organic molecules while being deposited as a film.

The present disclosure provides a method of in-situ monitoring photoactive organic molecules in real time while depositing a film of the photoactive organic molecules from a gas-phase state onto a substrate in a deposition processing chamber. The deposition process can be an OVPD or a VTE process. In this method, a radiation such as laser is used to excite the photoactive organic molecules in gas phase in the deposition processing chamber which causes the organic molecules to emit light of characteristic wavelength by PL, fluorescence or phosphorescence, i.e., PL emission. The PL emission is measured in-situ and in real time at the respective characteristic wavelength. Based on the intensity of the PL emission, the concentration level of the photoactive organic molecules in the processing chamber can be determined. Because the PL emission is measured in-situ without disturbing the deposition process and in real time, the concentration level can be determined in-situ and in real time as the deposition process is in progress.

The references to PL emission made in this disclosure will be understood to encompass any emission of either fluorescence or phosphorescence, or combinations. Reference to "photoactive" or "luminescent" organic gas made in this disclosure will be understood to encompass any organic materials, in any form, which can be vaporized, and can emit fluorescent or phosphorescent light, or combinations. The term "in situ" is used herein to mean examining a phenomenon exactly in place where it occurs. In other words, in the present context, the deposition process of the organic molecules in the process chamber is being examined using the PL spectroscopy method of the present disclosure without interrupting the normal operation of the deposition process.

Figure 17:
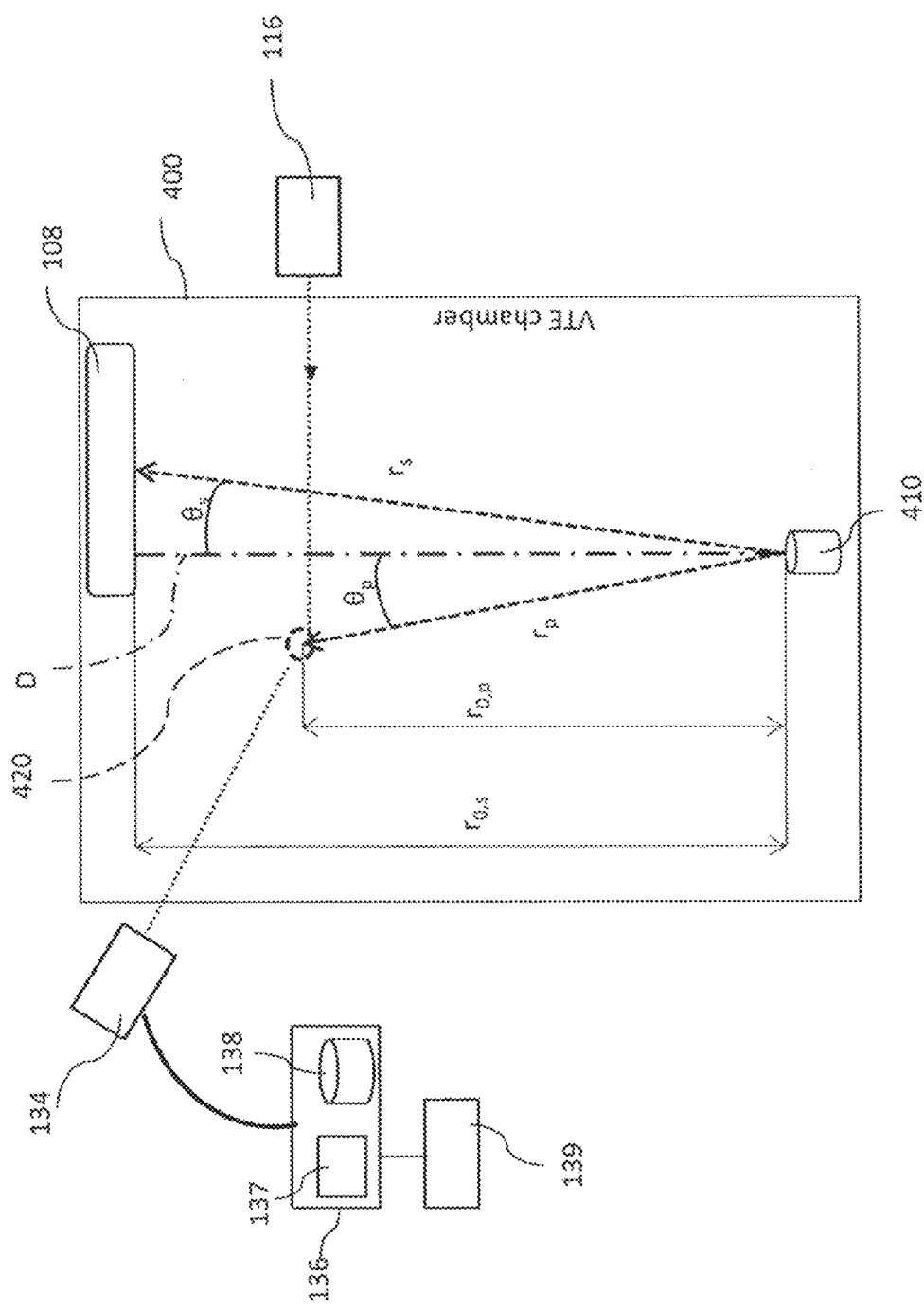
FIG. 17 is a schematic illustration of a vacuum thermal evaporation deposition chamber configured for in-situ monitoring organic molecules through photoluminescence emission according to another embodiment.

FIG. 1 is a schematic cross-section view illustrating an example of a system 100 for in-situ monitoring photoactive organic molecules through PL emission while a film of the organic molecules is being deposited from gas phase vapor onto a substrate 108 in accordance with some embodiments. The exemplary system comprises a processing chamber 102 in which the deposition of the gas-phase photoactive organic molecules onto a substrate 108 is carried out. Processing chamber 102 is configured to provide one or more organic materials in gas-phase to be deposited as a film on the substrate 108 within the processing chamber. The system configuration shown in FIG. 1 is applicable to any gas-phase deposition system, such as OVPD, VTE, CVD, etc. In FIG. 1, the substrate 108 is shown oriented facing up which is more typical of an OVPD process. Although the substrate is typically oriented facing down in a typical VTE process, as shown in FIG. 17, the general configuration showing the relationship among the irradiating light sources and the associated photodetectors are applicable to any gas-phase deposition process in the context of the present disclosure.

In an OVPD embodiment, a carrier gas such as nitrogen or a noble gas is used to transport one or more photoactive organic materials in gas phase into the processing chamber. In a VTE embodiment, the one or more photoactive organic materials are evaporated in a source crucible provided inside the processing chamber. (Not shown in FIG. 1). A stage 110 holds the substrate 108 inside processing chamber 102 during the deposition process.

The system 100 is provided with at least one radiation source 116 for irradiating the gas-phase photoactive organic molecules in the region above the substrate 108 in the processing chamber 102 and at least one detector 134 for measuring the intensity of the resulting PL emission from the gas-phase photoactive organic molecules.

The at least one radiation source 116 emits a beam of radiation 150 having an appropriate wavelength depending on the absorption spectrum of the gas-phase photoactive organic molecules being monitored. In one preferred embodiment, the at least one radiation source 116 is a laser beam having an appropriate wavelength. In order to monitor the deposition process of the one or more gas-phase organic materials in the processing chamber 102, the beam of radiation 150 is directed into the processing chamber 102 through an optical viewing port 124 for irradiating the one or more gas-phase organic materials during the deposition process. The beam of radiation 150 can be cleaned using a spatial filter 117 and focused using an appropriate set of optical lenses 118. If necessary, an optical chopper 120 and a mirror 122 also can be provided. The mirror 122 can be an actuated mirror so that direction of the radiation beam 150 can be automatically controlled. When the beam of radiation 150 irradiates the one or more gas-phase organic materials inside the processing chamber 102, the molecules of the organic materials absorb the radiation and are excited in real time and in-situ during the deposition process, and generate PL emission 152.

The at least one detector 134 can be located inside, outside or on the wall of the processing chamber 102, and measures the intensity of the PL emission 152. The at least one detector 134 can be photodetectors or spectrometers. Because the spectrum of the PL emission 152 depends on the nature of the particular photoactive organic material being excited, the at least one detector 134 can comprise at least one photodetector adapted for detecting the PL emission 152 at a preselected characteristic wavelength corresponding to the particular gas-phase organic materials being monitored and the number of the photodetectors will correspond to the number of gas-phase organic materials being monitored.

An optical viewing port 128 on processing chamber's wall 104 provides a pathway for the PL emission 152 to reach the detector. Accessories such as lenses 130 and a spectral filter 132 can be provided in the pathway of the PL emission 152 to filter out the radiation 150 from the radiation source 116. By means of finely adjusted optical lenses, a fraction of the light emitted in a region of interest is captured, and directed through a long pass filter, such as the spectral filter 132, towards the at least one detector 134. The long pass filter is used to filter out light from the source considering the Stokes shift that yields a lower frequency PL emission. If the light source is modulated, a lock-in amplifier is used to read the signal from the photodetector and remove all parasitic frequencies. This measurement provides PL emission intensity in a chosen region of the processing chamber for monitoring processing parameter in real time and in-situ. Additionally, a light trap 126 provided inside the processing chamber 102 blocks and absorbs the radiation beam 150 after the radiation beam has passed through the gas-phase organic material and prevents the radiation beam from scattering inside processing chamber.

The hardware components surrounding the process chamber 102, such as the at least one radiation source 116, the at least one detector 134 and the various optical components shown in FIG. 1 can be mounted or supported on an appropriate supporting structure such as support struts 114 as shown in FIG. 1.

Figure 2:
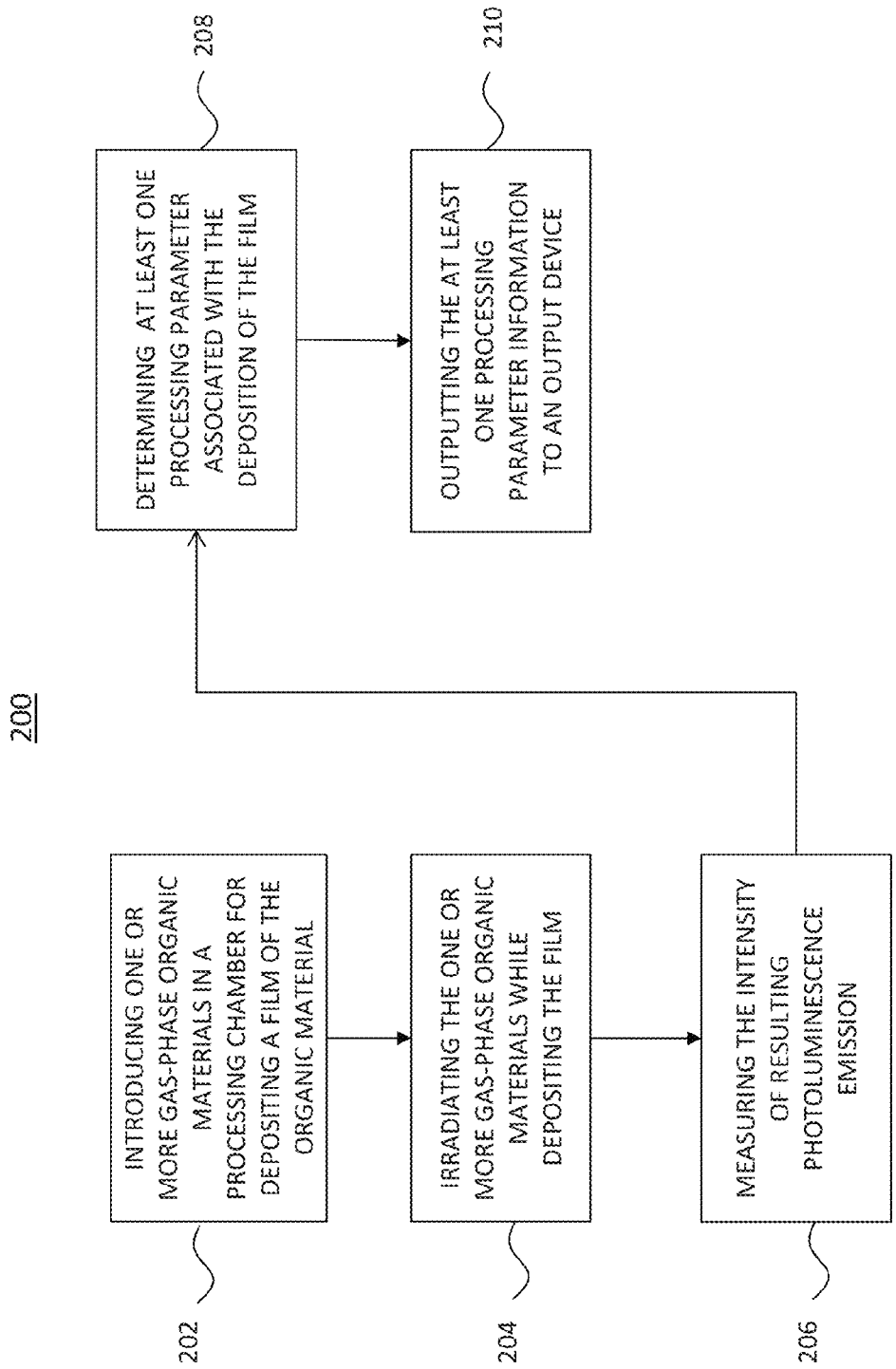
FIG. 2 is a flow chart diagram illustrating a method of in-situ monitoring organic molecules according to some embodiments.

FIG. 2 is a flow chart 200 illustrating the method of monitoring photoactive organic molecules in-situ through PL emission while depositing a film of the organic materials according to an embodiment. The method comprises introducing one or more gas-phase photoactive organic materials into the processing chamber 102 for depositing the film of the organic materials on a substrate 108 in the processing chamber 102. (See box 202). Generally, the one or more photoactive organic materials are in the form of liquid or solid, which are evaporated and introduced into the processing chamber 102 in a gas-phase state.

Next, the one or more gas-phase photoactive organic materials in the processing chamber 102 is irradiated with a radiation from at least one radiation source 116, 116a in real time and in-situ while depositing the film of the one or more gas-phase photoactive organic materials, thereby generating a PL emission 152, 152a from each of the one or more photoactive organic materials. (See box 204). In one embodiment, the irradiation is conducted using a laser beam so that the laser beam can be pointed to a particular region inside the processing chamber for monitoring.

The intensity of the PL emission from each of the one or more photoactive organic materials is measured. (See box 206). Then, from the measured intensity of the PL emission, the method determines the concentration level of the one or more gas-phase photoactive organic materials using the concentration calibration factor $k_c$. (See box 208). In another embodiment, the deposition rate of the film is determined from the concentration level. (See box 210). The method described in this disclosure further comprises outputting from the microprocessor 137 the at least one processing parameter associated with depositing the at least one photoactive organic gas, in accordance with some embodiments. The microprocessor 137 is connected with the at least one photodetector. Such an outputting step may comprise displaying the at least one processing parameter on the output device 139.

Figure 3:
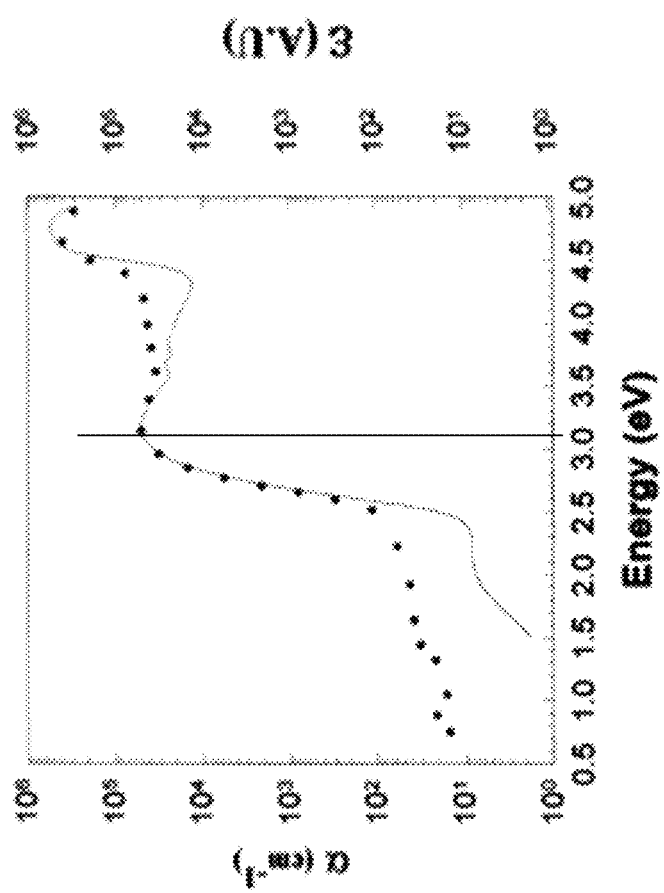
FIG. 3 illustrates the photoluminescence spectrum of an example photoactive organic molecule Alq3 in solution (solid line).

In accordance with some embodiments, the radiation source 116 is chosen to match the absorption profile of the molecules of the photoactive organic gas. For example, FIG. 3 illustrates the PL spectrum of an exemplary photoactive organic molecule Alq3 in solution (solid line) reported in the literature. The peak absorption of Alq3 in solution is at about 3.1 eV. If a laser with 100 mW diode pumped at 405 nm is used, the photon energy, $\epsilon_{photon}$, is 3.1 eV matching with the profile of Alq3. In consequence, the rate of photons emitted by the diode laser, $\dot{N}_0$, is about $2 \times 10^{17}$ photons/second, as shown by the calculations as follow:

$$\varepsilon_{photon} = 4.95 \times 10^{-19} J = 3.1 eV \qquad (1)$$

$$\dot{N}_0 = \frac{0.100 W}{5 \times 10^{-19} J} = 2 \times 10^{17} \, photons/s \qquad (2)$$

Based on the curve of FIG. 3, absorption coefficient, a, of Alq3 is about $6.8 \times 10^{-5}$ cm$^{-1}$ at about 380-400 nm. If assuming the length, $l_{pr}$, of chamber imaged onto the detector (x) is about 114 mm, the photon absorption rate $\dot{N}_{abs}(x)$ is about $1.6 \times 10^{14}$/second (s), as shown by the calculations as follow:

$$N(x) = N_0 e^{-\alpha x} \rightarrow \dot{N}_{abs}(x) = 1.6 \times 10^{14} s^{-1} \qquad (3)$$

where $l_{pr}$ is the length of the monitored region 154 that is the length in the processing chamber 102 that is being imaged by the photodetector 134. In this calculation, $l_{pr}$ is set to 114 mm. Furthermore, the linear absorption density rate $\dot{\lambda}$ in the monitored region 154 is defined as:

$$\dot{\lambda} = \frac{\dot{N}_{abs}}{l_{pr}} = 1.4 \times 10^{12} / mm \cdot s \qquad (4)$$

Figure 4:
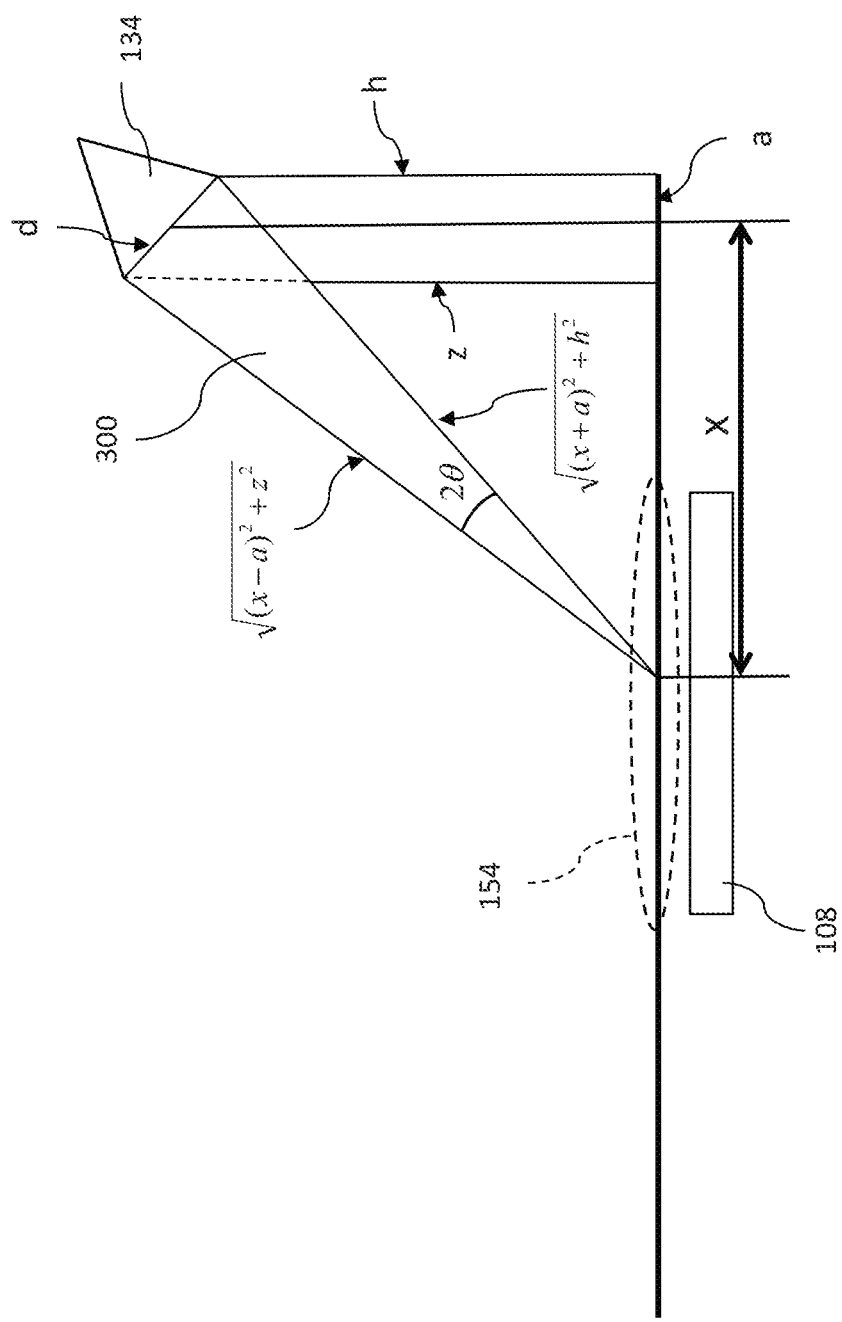
FIG. 4 is a schematic diagram illustrating the geometric relationship of the PL emission detector and the region inside the processing chamber being monitored.
Figure 5:
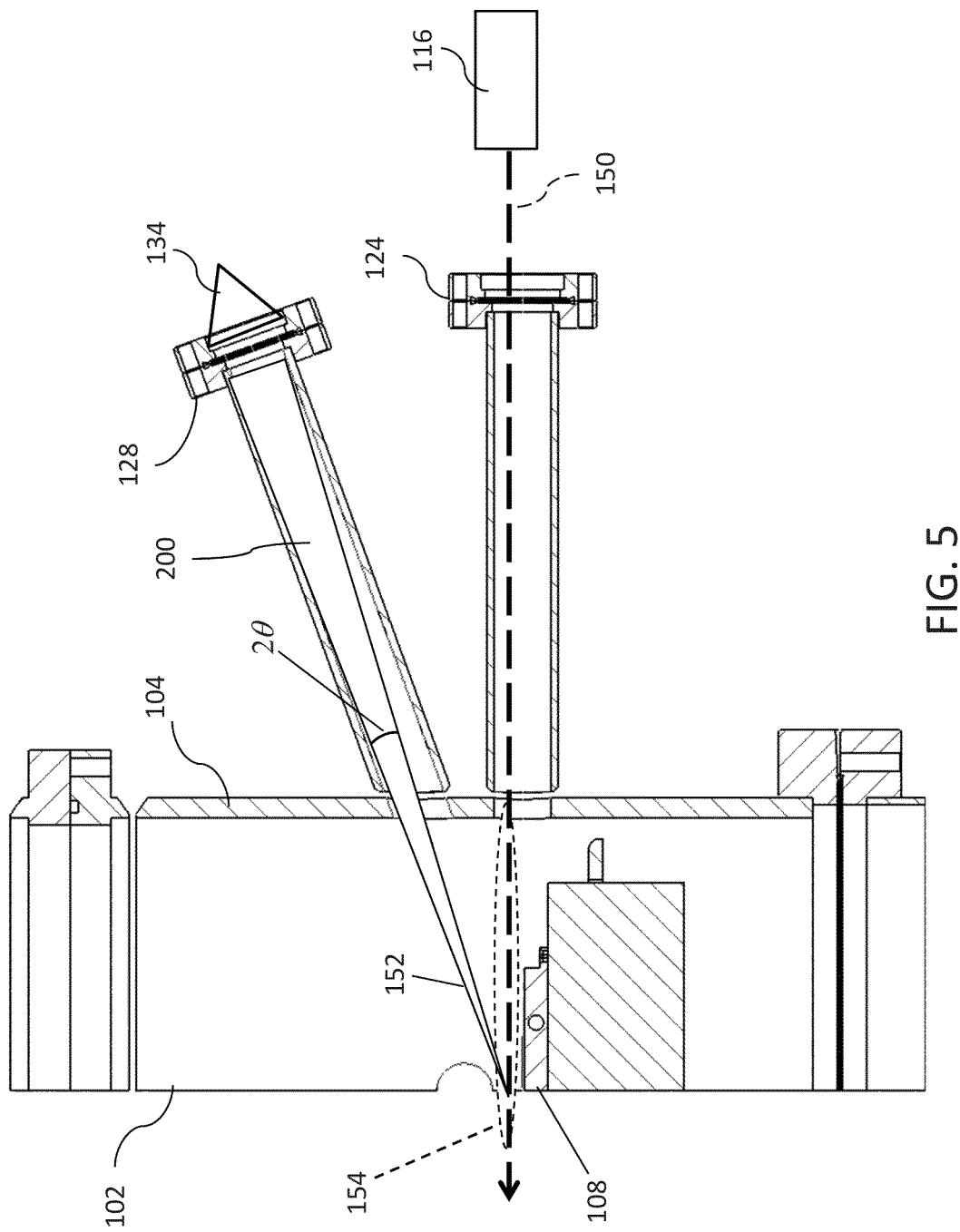
FIG. 5 is a schematic cross section diagram illustrating a portion of a processing chamber configured according to the present disclosure.

FIG. 4 is a schematic diagram illustrating the geometric relationship between the monitored region 154 of gas-phase photoactive organic materials just above the substrate 108 and the photodetector 134 for purpose of calculating the photon capture rate (PL intensity) $\dot{\sigma}$ at photodetector 134. FIG. 5 is another schematic diagram showing the geometric relationship overlaid with a cross section illustration of the processing chamber 102. The optical port 124 through which the radiation beam 150 enters the processing chamber 102 and the second optical port 128 through which the photodetector 134 captures/detects the PL emission 152 are shown. The monitored region of the gas-phase photoactive organic materials is identified by the region labeled as 154 and the radiation beam 150 is directed to that region 154. In the illustrated example, the monitored region 154 is a region close to the substrate 108 in order to monitor the condition of the gas-phase photoactive organic materials as they are being depositing on the substrate 108.

In other embodiments, where the concentration level of the gas-phase organic materials in the processing chamber 102 far away from the substrate 108 is desired, the radiation beam 150 can be directed to a region away from the substrate 108 to monitor the characteristics of the gas-phase organic materials in that region. Using a concentrated radiation source such as lasers, allows a high degree of spatial resolution because the system can be configured to point the laser beam to any region inside the processing chamber for monitoring the characteristic parameter of the one or more gas-phase photoactive organic materials in that particular region. Such spatial resolution can be utilized, for example, to map the distribution of local concentration levels of the one or more gas-phase photoactive organic materials inside the processing chamber.

With the help of FIGS. 4 and 5, the photon capture rate (PL intensity) $\dot{\sigma}$ at the detector 134 can be calculated as follows:

$$\dot{\sigma} = \int_{l_{pr}} \dot{\lambda}(x) \Phi_{PE} \eta_{det}(x) dx \qquad (5)$$

$$\eta(x) = \frac{\Omega(x)}{4\pi} \qquad (6)$$

$$\Omega = 2\pi(1 - \cos\theta) \qquad (7)$$

-continued $$\dot{\sigma} = \frac{\lambda}{2} \int_{l_{pr}} \left( 1 - \frac{1}{2}\sqrt{\frac{((x-a)^2 + z^2) + ((x+a)^2 + h^2) - d^2 + 2\sqrt{(x-a)^2 + z^2}\sqrt{(x+a)^2 + h^2}}{\sqrt{(x-a)^2 + z^2}\sqrt{(x+a)^2 + h^2}}} \right) \Phi_{PE} dx \quad (8)$$

where, $\dot{\sigma}$ is captured photons (PL intensity) in the window of optical port 128;

$\eta_{det}(x)$ is capture ratio at a specific location;

$\Phi_{PE}$ is the photoemission quantum yield;

$\Omega$ represents the solid angle of a cone 300 defined by a point source of PL emission in the monitored region 154 and the photodetector 134; and $\dot{\lambda}$ is the linear absorption density rate of the organic molecules being monitored. It is defined by Equation (4).

Assuming a photoluminescence quantum yield $\Phi_{PE}$ of 100%, each photons captured in the monitored region 154 gives rise to photoemission. Using the value of $\dot{\lambda}=1.4\times10^{12}$ photons/second found in Equation (4) for the linear absorption density, the amount of photons emitted in the monitored region 154 and captured at the window of the detector is $\dot{\sigma}=5.36\times10^{10}$ photons/second, calculated using Equation (8). Taking into account losses of typical special filter, for example, 15% of losses, the actual captured photons (I) in the window of the detector is:

$$\Phi = \dot{\sigma} \cdot \gamma_{lpf} = \dot{\sigma} \cdot 85\% = 4.56\times10^{10} \text{ photons/second} \quad (9)$$

where $\gamma_{lpf}$ is the rate of photons passing the special filter. Typical organic luminescent molecule such as Alq3 has photo energy of $4\times10^{-19}$ J/photon. So the incident power on the photodetector $P_{fl}$ is:

$$P_{fl} = (4.56\times10^{10} \text{ photons/s}) \times (4\times10^{-19} \text{ J/photon}) = 18 \text{ nW}.$$

In some embodiments, the method of the present disclosure encompasses monitoring the organic materials while a mixture of two or more gas-phase photoactive organic materials are being co-deposited. As mentioned above, because the spectrum of the PL emission 152 depends on the nature of the particular photoactive organic material being excited, the system 100 is then provided with two or more photodetectors each being the appropriate type configured for detecting the PL emission from one particular gas-phase organic material being deposited and monitored. For example, FIG. 1 shows a second photodetector 134a for measuring the intensity of the second PL emission 152a from a second photoactive organic material. The second photodetector 134a can be accompanied by appropriate accessories such as filters or lenses represented by 130a. The filters/lenses 130a function as a spectral filter allowing the desired spectrum of the second PL emission 152a to reach the second photodetector 134a while filtering out the spectrum of the first PL emission 152. Similarly, the filters/lenses 130, 132 of the first photodetector 134 allows the spectrum of the first PL emission 152 to reach the first photodetector 134 while filtering out the spectrum of the second PL emission 152a. The process chamber 102 is provided with a second optical port 128a for guiding the second PL emission 152a to the second photodetector 134a.

In some embodiments, at least one detector can comprise a spectrometer. A spectrometer readily detects a spectrum of the PL emission from the one or more gas-phase photoactive organic materials and the contribution of each probed gas-phase organic species can be isolated from such spectra according to their characteristic PL emission wavelength.

Furthermore, in order to maximize the PL emission by the gas-phase photoactive organic materials being monitored, the radiation source 116 is chosen to match the photo-absorption profile of the molecules of the photoactive organic materials. "Photo-absorption profile" in this context refers to the range of wavelengths of light in which the photoactive organic materials' PL emission is the most efficient. In other words, in that range of wavelengths of light, the intensity of PL emission generated for every photon incident on the photoactive organic material is the greatest. Therefore, depending on the particular photoactive organic materials being co-deposited and being monitored, more than one radiation source may be necessary in order to match the emission spectrum of the radiation sources to the photo-absorption profiles of the one or more photoactive organic materials being monitored. For example, FIG. 1 shows a second radiation source 116a for generating a second beam of radiation 150a that has a different wavelength than the first beam of radiation 150. The second radiation source 116a can be accompanied by a second set of a spatial filter 117a, optical lenses 118a, an optical chopper 120a, and a mirror 122 as appropriate.

System 100 can comprise a central processing unit 136 that is connected to the photodetectors 134, 134a for processing the measured PL emission data. Central processing unit 136 can be a computer configured with an appropriate data processing hardware and software for performing the data processing operations. Central processing unit 136 can have a microprocessor 137, an appropriate type of data storage unit 138 and an output device 139. Some examples of an output device 139 are a display monitor and/or a printer. The microprocessor 137 performs the data processing operations using the measured PL emission data according to the method of the present disclosure and can display the results on the output device 139 or store the data in the data storage unit 138 for subsequent use by central processing unit 136.

In a preferred embodiment, the PL emission monitoring described herein is laser induced fluorescence monitoring. And for practical applications, laser induced fluorescence monitoring requires a fluorescence signal level that is high enough for detection without compromising the spatial resolution ensured by the laser light confinement. The optical power of detected light $\chi_{det}$ is given by:

$$\chi_{det} = I(v)A_L(1 - e^{-\alpha l})\phi_{FL}\frac{\Omega}{4\pi}\eta_{det} \quad (10)$$

where I(v) is the incident laser irradiance, $A_L$ is the cross-sectional area of the beam, l is the length of the probe region, $\alpha$ is the absorbance given by the product of $N_1$, the population of organic molecules in ground state of lowest electronic energy, and $\sigma_{12}(v)$, the absorption cross-section of the irradiated transition at laser frequency. Thus, $N_1$ is directly relates to the concentration of emitting organic molecules $c_{org}$. $\phi_{FL}$ is the fluorescence quantum yield, $\Omega$ is the collection solid angle, and $\eta_{det}$ is the detection efficiency taking into account losses due to filtering, optics, and quantum efficiency of the detector.

Equation (10) can be simplified further in the low-pressure, low-concentration gaseous environment in the deposition system of the present disclosure. Since only a small fraction of light is absorbed inside the chamber, the argument of the exponential is much smaller than unity. Therefore, upon expansion, Equation (10) simplifies to:

$$\chi_{det} = I(v)A_L l N_1 \sigma_{12}(v) \cdot \phi_{FL} \cdot \frac{\Omega}{4\pi} \eta_{det} \qquad (11)$$

Consequently, this relationship shows that the detected fluorescent emission light evolves linearly with the solute concentration represented in Equation (11) by the organic molecules population in the lower state of the probed transition $N_1$. The above discussions are applicable to all vapor phase deposition processes.

The PL monitoring method described in the present disclosure can be used to monitor in-situ and real-time process variables of a gas phase deposition process of photoactive organic species. The deposition rate $r_{dep}$ of organic species on the substrate 108 and the concentration of organic species $c_p$ in the process chamber 102 are such process variables. In order to evaluate continuously these process variables, these are linked to the measured photoluminescence intensity $P_{PL}$ through conversion or tooling factors $k_r$ and $k_c$:

$$r_{dep} = k_r (P_{PL} - P_{PL,baseline}) \qquad (12)$$

$$c_p = k_c (P_{PL} - P_{PL,baseline}) \qquad (13)$$

where
- $k_r$ is the deposition rate conversion factor;
- $k_c$ is the concentration conversion factor;
- $P_{PL}$ is the measured photoluminescence intensity incident on the photodetector 134;
- $P_{PL,baseline}$ is the average baseline intensity in the processing chamber detected by the photodetector before any photoactive organic materials for the deposition process is introduced into the processing chamber. $P_{PL,baseline}$ represents the background PL emission signal in the processing chamber generated by the presence of some organic material condensed somewhere inside the processing chamber. This quantity is measured before a deposition process, for example, during a calibration process, and the central processing unit 136 stores the value. $P_{PL,baseline}$ can be measured by taking a measurement over a predetermined duration, e.g. one minute, in the absence of any organic species in the flow then averaging the detected PL emission intensity values.

Equation (11) shows that the intensity of the light incident on the photodetector 134 is proportional to the gas phase concentration of organic photoactive species in the process chamber 102. But the terms in Equation (11) are not easily accessible and the quantitative evaluation of the concentration level $c_p$ from the measured photoluminescence signal is not straightforward. It requires a calibration relying on a measurable quantity that is representative of the concentration of photoactive organic species in the chamber. The thickness of a film of photoactive organic species deposited on a sacrificial sample is such a measurable. Dividing this thickness by the deposition time delivers the deposition rate of photoactive organic species $r_{dep}$. In consequence, simultaneous and independent measurements of $P_{PL}$ and $r_{dep}$ can be used to calibrate the deposition system and to calculate the conversion factors $k_r$ and $k_c$. This procedure requires that the relationship between $r_{dep}$ and $c_p$ is known for the considered processing system. This relationship is linear, validating the use of Equation (12) since $r_{dep} \propto c_p \propto P_{PL}$.

A calibration procedure that aims at finding the deposition rate conversion factor $k_r$ requires experimental determination of the deposition rate $r_{dep,exp}$ in order to solve the following relation:

$$k_r = \frac{r_{dep,exp}}{P_{PL} - P_{PL,baseline}} \qquad (14)$$

In the same line, a calibration procedure that aims at finding the concentration conversion factor $k_c$ requires experimental determination of the concentration level $c_{p,exp}$ in the monitored region in order to solve the following relation:

$$k_c = \frac{c_{p,exp}}{P_{PL} - P_{PL,baseline}} \qquad (15)$$

The following paragraphs show how the conversion factors $k_r$ and $k_c$, and the relationship between $r_{dep}$ and $c_p$ are determined for two different processing systems, OVPD and VTE:

Calibration for VTE Processing Chambers

Referring to FIG. 17, a schematic of a VTE deposition processing chamber 400 configured with appropriate PL emission monitoring system components for probing and monitoring the photoactive organic materials inside the VTE deposition processing chamber 400 is shown. The processing chamber 400 is provided with PL emission monitoring system components described above in connection with the processing chamber 102 but for illustrative purposes, only some key components are schematically shown. For example, the VTE deposition processing chamber 400 is provided with at least one radiation source 116, such as a laser light source, for irradiating the photoactive organic materials inside the VTE chamber and at least one detector 134 for detecting the resulting PL emission emanating from the irradiated photoactive organic materials. The various accessory components relating to the radiation source 116 and the detector 134 discussed above are equally applicable to this VTE embodiment including the additional radiation source 116a and the detector 134a. Additionally, the VTE embodiment system can also comprise the central processing unit 136, the microprocessor 137, the data storage unit 138 and the output device 139 as described above.

In the case of VTE, the deposition rate conversion factor $k_r$ is empirically determined through a tool calibration procedure. The calibration procedure involves depositing a film of the photoactive organic material on a sacrificial calibration substrate in the VTE chamber 400 with known constant processing conditions. This film will be referred to herein as a calibration film. The deposition rate $r_{dep,exp}$ of the calibration film is determined subsequently by dividing the calibration film's thickness by the deposition time. The corresponding PL intensity $P_{PL}$ is determined by taking the average of the signal measured by the detector 134 during the deposition of the calibration film. The deposition rate conversion factor $k_r$ is then given by Equation (14) as the ratio of $r_{dep,exp}$ to ($P_{PL} - P_{PL,baseline}$). The deposition rate conversion factor, $k_r$, shows a complex dependence on the following geometric factors: the position of the substrate 108 relative to the evaporation source 410; the location of the monitored region 420 (the small local area inside the VTE chamber which is irradiated by the radiation beam and the target of the detector 134 for measuring the PL emission emanating therefrom) relative to the evaporation source 410; and the position of the detector 134 relative to the monitored region 420.

VTE Process

In VTE, the flux $J(r,\theta)$ of the photoactive organic material in the chamber 400 is dependent on the position relative to the evaporation source crucible 410 because the flux decreases as the square of distance from the evaporation source. The flux $J(r,\theta)$ scales as such:

$$J(r,\theta) = \dot{n}\frac{\cos^2\theta}{r^2} = \dot{n}\frac{r_0^2}{r^4} \tag{16}$$

where $\dot{n}$ is proportional to the flow rate of the photoactive organic material evaporated by the source crucible 410. $\theta$ represents the angle to the point of interest with respect to the axis of effusion D of the vapor from the evaporation source crucible 410. Thus, the angle to the substrate 108 with respect to the axis of effusion D is represented by the angle $\theta_S$. The angle to the monitored region 420 with respect to the axis of effusion D is represented by the angle $\theta_p$. r represents the distance from the evaporation source crucible 410 to the point of interest. Thus, the distance from the evaporation source crucible 410 to the substrate 108 is represented by the arrow $r_s$ and the distance from the evaporation source crucible 410 to the monitored region 420 is represented by the arrow $r_p$. $r_0$ is the distance from the evaporation source crucible 410 to the considered point along the effusion axis D.

Assuming that the deposited film covers the substrate completely and uniformly, the flux $J_{dep}$ on the substrate is then given by:

$$J_{dep} = \dot{n}\frac{r_{0,s}^2}{r_s^4} = r_{dep}\rho_{org} \tag{17}$$

where $r_s$ is the distance from the evaporation source crucible 410 to the center of the substrate, $r_{0,s}$ is the distance from the evaporation source crucible 410 to the surface of the substrate 108 along the effusion axis D, and $\rho_{org}$ is the molar density of the organic material deposited onto the substrate (i.e., the condensed solid phase of the organic material). On the other hand, the flux $J_p$ of photoactive organic materials traversing the monitored region 420 being monitored by the detector 134 is given by:

$$J_p = \dot{n}\frac{r_{0,p}^2}{r_p^4} \tag{18}$$

where $r_p$ is the distance from the evaporation source crucible 410 to the center of the monitored region 420, and $r_{0,p}$ is the distance from the evaporation source crucible 410 to the monitored region 420 along the effusion axis D. The concentration $c_p$ of photoactive organic material at the monitored region 420 is the ratio between the local flux $J_p$ and the mean molecular velocity v of the photoactive organic material:

$$c_p = \frac{J_p}{\bar{v}} \tag{19}$$

Assuming a Maxwellian distribution of molecular energies, the mean molecular velocity is constant and can be approximated by:

$$\bar{v} = \sqrt{\frac{3k_b T_{sc}}{m_{org}}} \tag{20}$$

where $k_b$ is the Boltzmann constant, $T_{sc}$ is the temperature of evaporation source crucible 410, $m_{org}$ is the mass of an individual molecule of organic material.

By combining the equations (17), (18) and (19), the concentration $c_p$ of photoactive organic material at the monitored region 420 can be expressed as a linear function of the deposition rate $r_{dep}$ of photoactive organic materials:

$$c_p = \frac{r_{0,p}^2 r_s^4}{r_p^4 r_{0,s}^2} \cdot \frac{\rho_{org}}{\bar{v}} \cdot r_{dep} \tag{21}$$

Combining Equation (21) to Equations (12) and (13) gives access to the evaluation of the concentration conversion factor $k_c$ from the empirically determined deposition rate conversion factor $k_r$ for VTE:

$$k_c = \frac{r_{0,p}^2 r_s^4}{r_p^4 r_{0,s}^2} \cdot \frac{\rho_{org}}{\bar{v}} \cdot k_r \tag{22}$$

Injecting $k_c$ into Equation (13), the concentration level $c_p$ at the monitored region 420 can be evaluated from the PL emission intensity $P_{PL}$ measured by the photodetector. Therefore, one can determine the local concentration of the photoactive organic materials at a monitored region 420 in-situ and in real-time by monitoring the PL emission while the VTE deposition is in process.

Using Equation (21), the concentration level $c_{p,exp}$ of the gas-phase photoactive organic material in the VTE processing chamber during the calibration of the VTE processing chamber can be determined. As discussed above, after obtaining the deposition rate $r_{dep,exp}$ of the calibration film, substituting $r_{dep}$ in Equation (21) with $r_{dep,exp}$, the concentration level $c_{p,exp}$ can be calculated.

Calibration for OVPD Processing Chambers

Figures 6, 7:
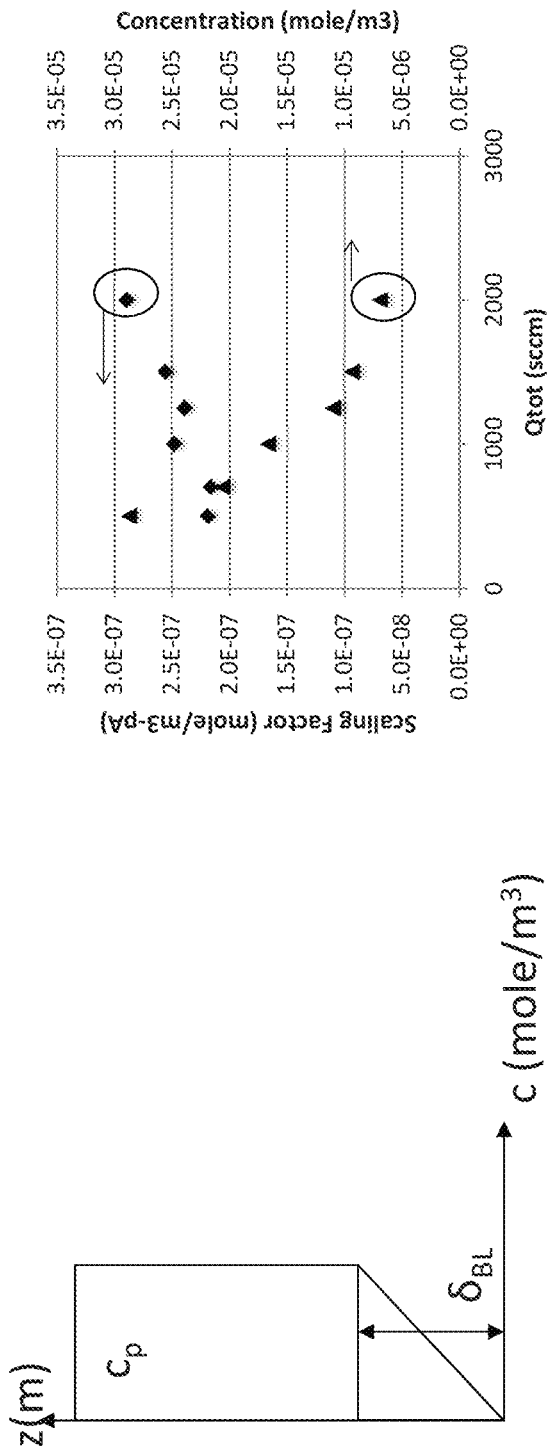
FIG. 6 is a schematic diagram for calculating concentration scaling factor from the PL intensity measurement based on Fick's diffusion law.
FIG. 7 is an exemplary plot illustrating concentration and scaling factor of a photoactive organic gas calculated from the PL emission intensity measurement based on Fick's diffusion law.

The OVPD technology is characterized by the use of a carrier gas to transport the evaporated organic molecules from the evaporation source to the cold substrate on which they condense to form a film. In steady-state, as the organic molecules diffuses and disperses in the carrier gas, the concentration of organic molecules in the processing chamber becomes uniform across the chamber after a sufficient travelling distance from the source. On the other hand, the carrier gas forms a boundary layer on top of the substrate through which the organic molecules must diffuse in order to condense on the substrate and form a film of a certain thickness. In consequence, the concentration of organic molecules monotonously decreases across this boundary layer. FIG. 6 is a diagram schematically illustrating the evolution of the organic molecules concentration in the OVPD processing chamber along a z-axis orthogonal to the substrate. As shown in the model of FIG. 6, the carrier gas forms a boundary layer having a thickness $\delta_{BL}$ on the substrate. Above the boundary layer, the concentration of organic molecules is constant at a value $c_p$.

In OVPD, the deposition rate conversion factor $k_r$ is empirically determined using a tool calibration procedure similar to the one used in VTE. The calibration procedure involves depositing a film of the at least one gas-phase photoactive organic material on a sacrificial calibration substrate in the OVPD chamber with known constant processing conditions. This film will be referred to herein as the calibration film. For a particular set of processing conditions, two measurements are taken for the calibration film. Firstly, the calibration film deposition rate, $r_{dep,exp}$, is calculated from the ratio of the film thickness to its deposition time. Secondly, during the calibration, the corresponding PL intensity $P_{PL}$ is determined by taking the average of the signal measured by the detector 134 during the deposition while irradiating the gas-phase organic material above the boundary layer thickness, i.e. in the monitored region, at a distance greater than $\delta_{BL}$ from the substrate. The deposition rate conversion factor $k_r$ is then given by Equation (14) as the ratio of $r_{dep,exp}$ to $(P_{PL}-P_{PL,baseline})$. For a given OVPD chamber geometry, the deposition rate conversion factor $k_r$ shows a strong dependence on processing conditions: the carrier gas temperature, the chamber wall and substrate temperature $T_r$ and $T_s$, the carrier gas total mass flow rate $Q_{tot}$ and the chamber background pressure $P_t$ all affect the diffusion process through the boundary layer and therefore affect the deposition rate for a given concentration above the boundary layer thickness. In consequence, a measured $k_r$ is only valid for the processing conditions used in its determination.

In OVPD, the linear relationship between the deposition rate $r_{dep}$ of organic species on the substrate 108 and their concentration $c_p$ in the processing chamber 102 above the boundary layer can be established using the Fick law that determines the diffusive flux across the boundary layer:

$$c_p = \frac{\delta_{BL}}{D_{org}} J_{dep} = \frac{\delta_{BL} \rho_{org}}{D_{org}} r_{dep} \tag{23}$$

where $c_p$ is concentration of a photoactive organic gas in the processing chamber;

$J_{dep}$ is the organic species flux onto the substrate;

$\delta_{BL}$ is the boundary layer thickness, the boundary layer being formed by the carrier gas on top of the substrate through which the organic molecules must diffuse in order to condense on the substrate and form a film of a certain thickness;

$D_{org}$ is diffusivity of organic molecules in the carrier gas;

$\rho_{org}$ is the molar density of the deposited organic material; and $r_{dep}$ is the film deposition rate onto the substrate;

Combining Equation (23) to Equations (12) and (13) gives access to the evaluation of the concentration conversion factor $k_c$ from the empirically determined deposition rate conversion factor $k_r$ for OVPD:

$$k_c = \frac{\delta_{BL} \rho_{org}}{D_{org}} k_r \tag{24}$$

Although the value of $k_r$ depends on processing conditions, the value of the concentration conversion factor $k_c$ shows little if no dependence at all on processing conditions. This is expected as processing conditions do not affect the relation embodied by Equation (11) between photoactive organic species concentration above the boundary layer and intensity measured by the photodetector 134. Injecting $k_c$ into Equation (13), the concentration $c_p$ in the monitored region 154 can be evaluated from the PL emission intensity $P_{PL}$ measured by the photodetector. Therefore, using this calibration method one can determine the local concentration of the one or more photoactive organic materials in the monitored region 154 in-situ and in real-time by monitoring the PL emission while the OVPD deposition is in process.

Using Equation (23), the concentration level $c_{p,exp}$ of the gas-phase photoactive organic material in the OVPD processing chamber during the calibration of the OVPD processing chamber can be determined. As discussed above, after obtaining the deposition rate $r_{dep,exp}$ of the calibration film, substituting $r_{dep}$ in Equation (23) with $r_{dep,exp}$, the concentration level $c_{p,exp}$ can be calculated.

An example of the calculation of $k_c$ during the calibration of the processing chamber in this method is illustrated in FIG. 7. FIG. 7 is an exemplary plot illustrating concentration and the calibration factor of a photoactive organic gas calculated from the PL intensity measurement based on Fick's diffusion law, as a function of total flow rate $(Q_{tot})$ of gases, mainly the carrier gas, in the processing chamber. The total flow rate is in the unit of standard cubic centimeter (sccm). The data shown in FIG. 7 was obtained as follows. With all other processing conditions kept constant, $Q_{tot}$ is systematically varied. For each value of $Q_{tot}$, the calibration method is applied by depositing a film of the photoactive organic species on a sample substrate and by simultaneously measuring the intensity of photoluminescence $P_{PL}$ emitted by the gas phase photoactive organic species in the monitored region 154 above the boundary layer. The corresponding deposition rate $r_{dep}$ of each film is evaluated using a thickness measurement. The values of $r_{dep}$ are then converted to concentrations of organic species above the boundary layer $c_p$ using Equation (23), the evolution of which is plotted in FIG. 7. For each value of $Q_{tot}$, the recorded $P_{PL}$, helps calculating $k_r$, using Equation (12). Finally, a corresponding value of $k_c$ is calculated using Equation (24), that is plotted vs. $Q_{tot}$ in FIG. 7. It shows a slight increase with $Q_{tot}$ where invariance is expected. This is due to the use of Fick law that provides a crude model of the diffusion across the boundary layer. During the calibration procedure, the systematic variation of a process parameter, such a $Q_{tot}$ in FIG. 7, helps evaluating $k_r$ over a broader range of organic species concentrations, increasing the accuracy of the final average value of the concentration conversion factor $k_c$.

Once the concentration conversion factor $k_c$ is determined for each photoactive organic material that will be monitored in-situ, the system 100 can be configured to determine the concentration level of the gas-phase photoactive organic material $c_p$ in real time from the measured intensity of PL emission $P_{PL}$. For example, the value of the concentration calibration factor $k_r$ can be stored in the data storage unit 138 and as the intensity of PL emission, $P_{PL}$, is measured during a deposition process, the microprocessor 137 can access the stored value of the concentration calibration factor $k_c$ and determine the corresponding $c_{bulk}$ value in real time by applying Equation (13).

The model based on the Fick's diffusion law described above is based on simplified assumptions and simple system geometry. In a preferred embodiment, finite element numerical modeling software can be employed to determine the concentration of a gas-phase photoactive organic material in a specific system.

Figures 8A, 8B:
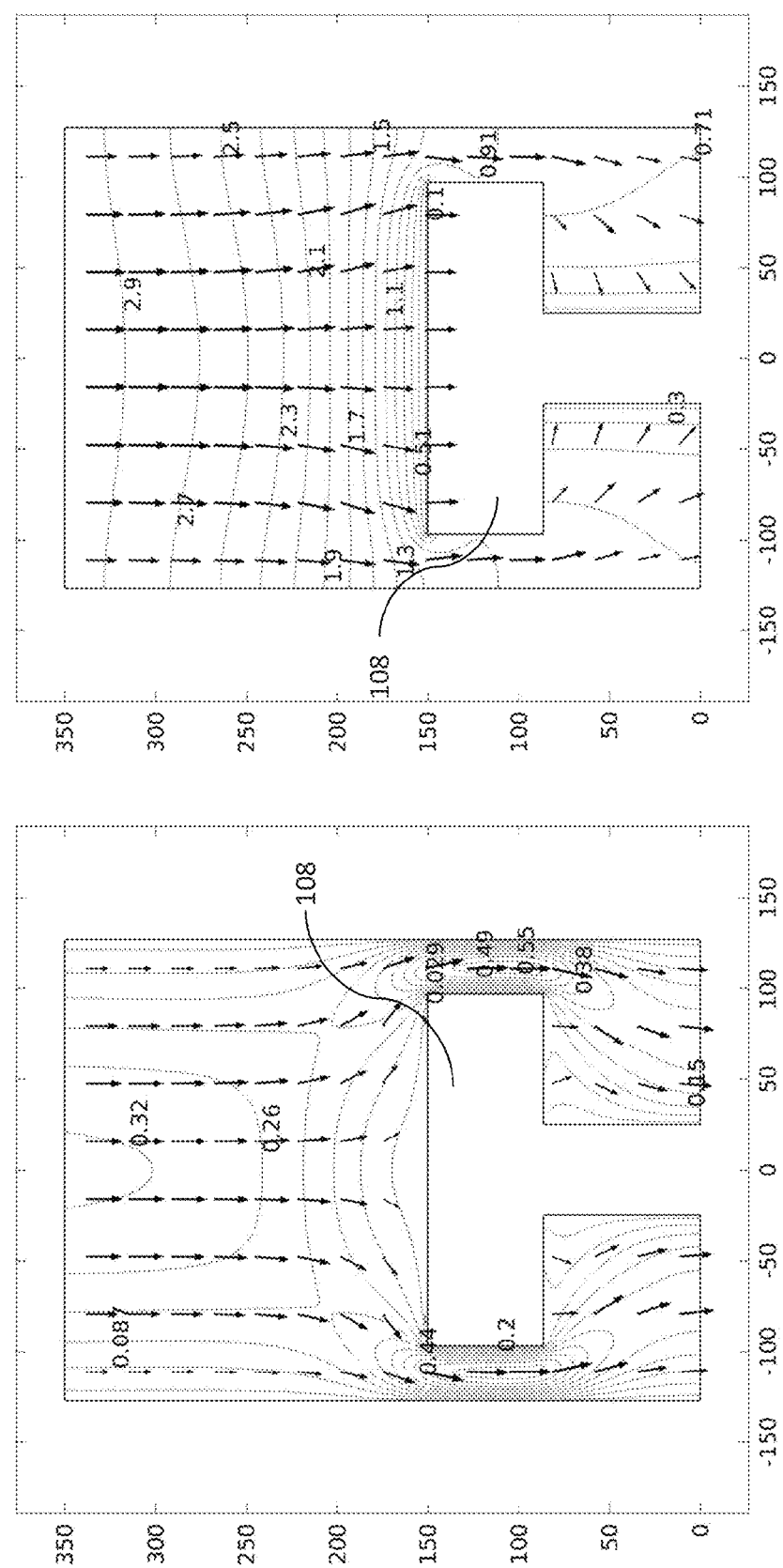
FIGS. 8A and 8B are schematic cross section diagrams of the processing chamber illustrating modeling results of the convective flux and concentration of a gas-phase photoactive organic material in the processing chamber.

FIGS. 8A and 8B are schematic cross section diagrams illustrating exemplary numerical modeling results of the convective flux and concentration of a gas-phase photoactive organic molecules in an OVPD processing chamber. In FIG. 8A, the contours and arrows represent the directions and velocity (in m/s) of carrier gas around the substrate holder of the OVPD system. In FIG. 8B, the contour lines represent concentration (in μmole/m³) of the gas-phase photoactive organic molecules, and the arrows represent total flux direction of the gas-phase photoactive organic molecules in the vicinity of the substrate holder of the OVPD processing chamber. The results are based on the PL emission measurement of the exemplary gas-phase photoactive organic molecules in the processing chamber in real time and in-situ.

The Fick's diffusion law Equation (23) uses a very crude one dimensional representation of the diffusion process across the boundary layer shown in FIG. 6. In reality, the carrier gas velocity field in FIG. 8A shows that the presence of sidewalls and the finite substrate area give a variation of the process parameters along the radial direction as well. Moreover, the convective and diffusive transport regions are intertwined, as can be seen from FIG. 8B that shows that an organic concentration gradient already develops far above the substrate in a region where convection still plays a dominant role. Finite element numerical modeling gives access to this complexity, allowing for a refinement of the relationship between measured deposition rate $r_{org}$ and concentration of organic species above the boundary layer $c_{bulk}$. For a set of processing conditions corresponding to the experimental conditions, the measured $r_{org}$ is set as the substrate boundary condition for the mass transport of organic species in the carrier gas. Finite element numerical modeling of the chamber then outputs a bulk concentration of organic species $c_{bulk}$ that matches this deposition rate. This numerical modeling calculation replaces the calculations done in Equations (24) and (23) by a more accurate model.

In the finite element modeling of the deposition chamber, the geometry of the deposition chamber is meshed into an aggregation of small finite elements. At each node of the mesh, different sets of equations are self-consistently solved. These equations are: a compressible Navier-Stokes set of equations that solves for the carrier gas flow, a thermal equation that solves for the heat transport and a convection-diffusion equation that solves for the mass transport in the chamber. A realistic representation of the system is achieved by using experimental processing conditions as the boundary conditions of these calculations.

By using finite element numerical modeling, more realistic representation of the deposition chamber can be achieved compared to the crude analytical models such as the first Fick's law. This allows representation of a more realistic relationship between the measured $r_{dep}$ and the corresponding $c_p$, allowing more accurate determination of the concentration calibration factor $k_c$ using Equation (24).

Figure 9:
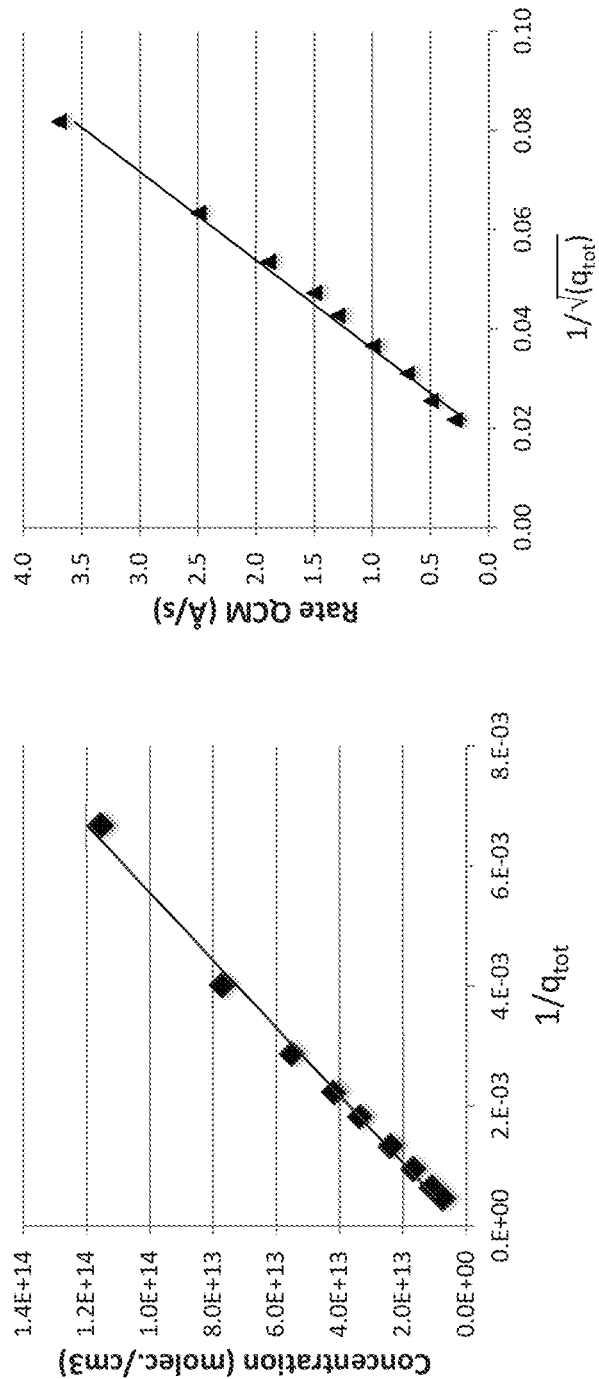
FIGS. 9-10 illustrate a comparison of measurements using both photoluminescence (PL) optical sensing and quartz crystal monitoring (QCM) organic molecules in an inert carrier gas in a processing chamber.
Figure 10:
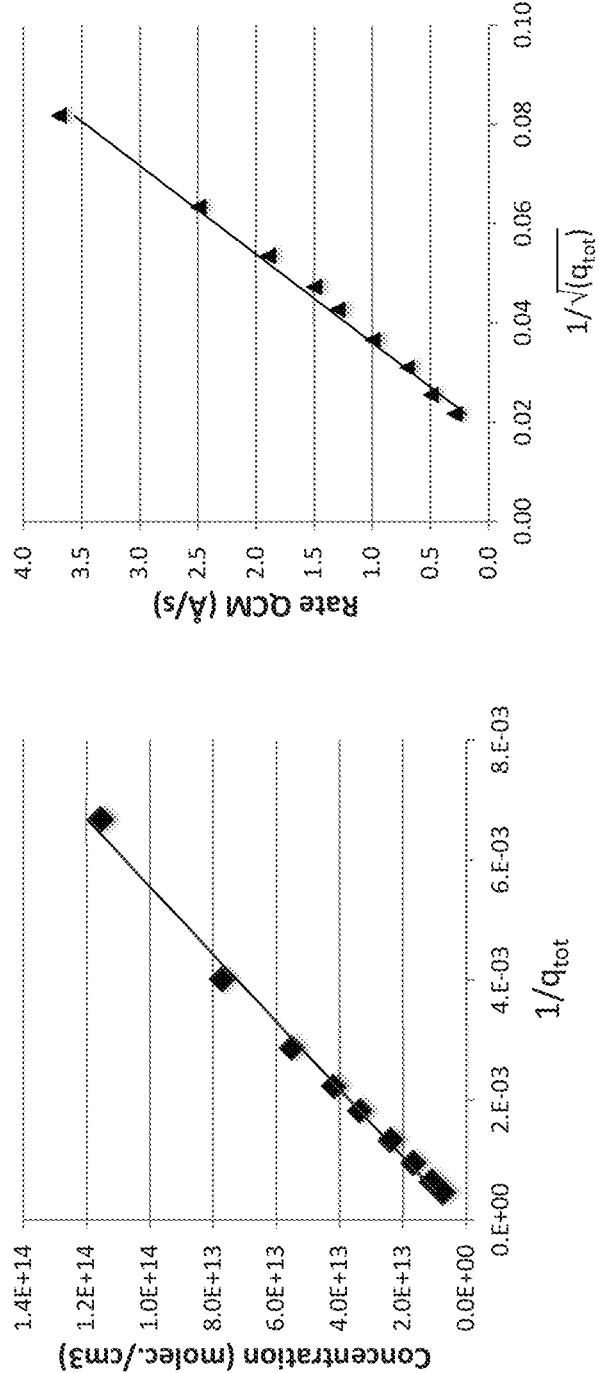

FIGS. 9-10 illustrate a comparison of the performance of PL emission monitoring and quartz crystal monitoring (QCM) of organic molecules in an inert carrier gas in a processing chamber. The measurements were made in an OVPD system, which entrains gas-phase photoactive organic molecules in an inert carrier gas $N_2$.

FIG. 10 shows the measurement of QCM sensing the photoactive organic molecule in the same inert carrier gas in a processing chamber based on a diffusive model. The QCM reading is based on the mass of the organic film deposited on a quartz crystal, and its dependence on the molar flow rate of the carrier gas, $Q_{tot}$ is modulated by the formation of a stagnant boundary layer of the carrier gas around the QCM monitor. The measured film deposition rate is proportional to square root of $Q_{tot}$. This dependence shows that the QCM interacts with the inert carrier gas. These interactions bring about thermo-mechanical fluctuations that disrupt the accurate QCM operation in a gaseous environment. In the design of a system with QCM measurement, constant replacement of the active crystal sensor is needed during regular use.

FIG. 9 shows the measurement of PL optical sensing a photoactive organic molecule in an inert carrier gas in a processing chamber based on a convective model. As a comparison, the concentration level measured based on the PL emission is in a linear relationship with $1/Q_{tot}$ showing that outside dilution, no other effect of the total carrier gas flow on the detection technique is present. This will improve measurement accuracy. Meanwhile, the radiation and the PL emission do not obstruct gas flow, and changes in flow conditions will not disrupt the accuracy of measurement in PL emission. Unlike the QCM measurement method, constant retooling is not needed in the PL emission measurement method of the present disclosure. A method for accurate and robust measurements is provided as described in the present disclosure. In both cases, molar flow rate of the photoactive organic gas was kept constant while adjusting the total flow rate $Q_{tot}$.

[Material Utilization Efficiency of OVPD Chambers]

The method described in the previous section to determine the deposition rate and concentration conversion factors $k_r$ and $k_c$ can be used to evaluate the material utilization efficiency $\eta_{ut}$ of each of the photoactive organic material in the OVPD chamber for different deposition process conditions. The material utilization efficiency, $\eta_{ut}$, refers to how efficiently the molecules of the one or more gas-phase photoactive organic materials diffuse across the carrier gas boundary layer formed on the substrate and condense or deposit on the substrate. It is an important figure of merit of the process, as higher material utilization efficiencies correspond to lower material consumption.

The material utilization efficiency $\eta_{ut}$ inside the OVPD processing chamber is formally described using equations (25), (26), and (30). Equation (25) below shows the relationship between the molar flow rate of the gas-phase photoactive organic molecules being transported by the carrier gas in the processing chamber, $\dot{n}_{ch}$, and the uniform concentration of the gas-phase photoactive organic molecules $c_p$ above the boundary layer inside the processing chamber:

$$\dot{n}_{ch} = c_p \frac{\dot{m}_{cg}}{\rho_{cg}} \tag{25}$$

where $\rho_{cg}$ is the density of the carrier gas; and $\dot{m}_{cg}$ is the mass flow rate of the carrier gas.

Equation (26) below shows the relationship between the molar flow rate of the gas-phase photoactive organic gas reaching the substrate $\dot{n}_{dep}$ and the deposition rate $r_{dep}$:

$$\dot{n}_{dep} = r_{dep} \rho_{org} A_{sub} \tag{26}$$

where $r_{dep}$ is the deposition rate of organic species on the substrate;

$\rho_{org}$ is the molar density of the photoactive organic material in solid phase; and $A_{sub}$ is the area of the substrate.

Equation (27) below shows that the characteristic material utilization efficiency, $\eta_{ut}$, is the ratio between the molar flow rate of the gas-phase organic molecules reaching the substrate and being deposited, $\dot{n}_{dep}$, and the molar flow rate of the gas-phase photoactive organic molecules in the processing chamber $\dot{n}_{ch}$:

$$\eta_{ut} = \frac{\dot{n}_{dep}}{\dot{n}_{ch}} = \frac{r_{dep}\rho_{org}A_{sub}\rho_{cg}}{c_p\dot{m}_{cg}} \quad (27)$$

Equation (27) can be modified by replacing $r_{dep}$ and $c_p$ by their values in Equations (12) and (13) respectively:

$$\eta_{ut} = \frac{k_r}{k_c}\frac{\rho_{org}A_{sub}\rho_{cg}}{\dot{m}_{cg}} \quad (28)$$

In consequence, the material utilization efficiency $\eta_{ut}$ can be determined directly from the knowledge of the conversion factors $k_r$ and $k_c$. $k_r$ varies with processing conditions (such as substrate temperature $T_{sub}$, chamber pressure $P_{ch}$, total carrier gas flow rate, $q_{tot}$, etc.) but its value is quickly obtained for each set of processing conditions from an ex-situ thickness measurement and the application of Equation (14), as described in the previous section.

Figure 11:
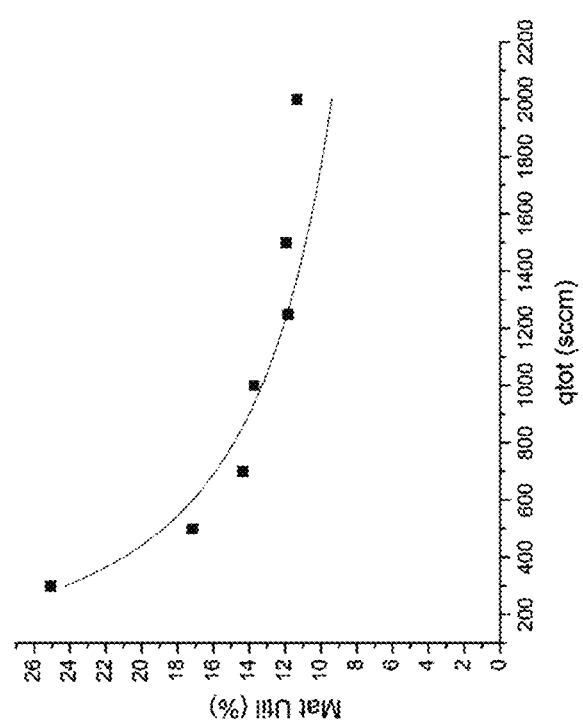
FIG. 11 shows an example plot of material utilization efficiency of a gas-phase photoactive organic material in an OVPD deposition process at various carrier gas flow rates.

The evaluation of Equation (28) for different sets of processing conditions provides a quick route to the determination and the optimization of the material utilization efficiency $\eta_{ut}$ of an OVPD chamber for the deposition of one or more photoactive organic species. FIG. 11 shows an exemplary plot of $\eta_{ut}$ evaluated using this method for several samples deposited at different total flow rates $q_{tot}$. The evolution of the value $\eta_{ut}$ with different process parameters such as $q_{tot}$, $P_{ch}$ and $T_{sub}$ then can be stored in the data storage unit 138 of the central processing unit 136.

The mapping of the material utilization efficiency $\eta_{ut}$ over different processing conditions can serve a second purpose. It can speed up the determination of the deposition rate conversion factor $k_r$ used to monitor in-situ and real-time the deposition rate $r_{dep}$ of photoactive organic species in an OVPD chamber by means of Equation (12). Indeed, the application of Equation (12) to determine $r_{dep}$ requires the knowledge of $k_r$ for the set of processing conditions. $k_r$ could be determined from the process parameters independent $k_c$, using Fick's law embodied in Equation (24). But this method is crude and the parameters in Equation (24) are not easily accessed. Alternatively, Equation (28) can be used that relies on the knowledge of the material utilization efficiency $\eta_{ut}$ over different processing conditions. Such a mapping of $\eta_{ut}$ can be acquired beforehand using the method above for an OVPD chamber.

In consequence, the method described in the present disclosure can be used to monitor the deposition rate, $r_{dep}$, of the photoactive organic material in an OVPD processing chamber in-situ and in real time during the deposition process. Because the characteristic material utilization rate $\eta_{ut}$ is already known, one can calculate beforehand the deposition rate conversion factor $k_r$. Then, during a deposition process being monitored in-situ and real-time, the PL emission intensity measured in real time $P_{PL}$ gives access to the deposition rate of photoactive organic species $r_{dep}$ on the substrate by the application of Equation (12). The central processing unit 136 would be configured with programs that enable the microprocessor 137 to execute these calculations using the Equations (28) and (12). The $r_{dep}$ value can be output to the output device 139 or stored in the storage unit 138.

Dynamic Perturbation Monitoring

In the embodiments described above, determining the at least one processing parameter such as concentration, $c_p$, of the organic material in the processing chamber, and the deposition rate, $r_{dep}$, of the organic material are performed in a steady state of depositing the organic film in the processing chamber. However, in some other embodiments, determining the at least one processing parameter can also be performed when the conditions in the deposition processing chamber is in a non-steady dynamic state. In other words the at least one processing parameter can be monitored in situ and in real time to detect any dynamic perturbations in the deposition processing condition.

Mass transport of the at least one photoactive organic material with a carrier gas in an OVPD processing chamber at a non-steady state can be described by the theories and equations that describe convection-diffusion phenomena known to those of ordinary skill in the art. For example, the laminar flow rate of the carrier gas can be calculated according to the following equation:

$$\bar{u}_{cg} = \frac{\dot{m}_{cg}}{\rho_{cg}\pi a^2} \quad (29)$$

where
$\bar{u}_{cg}$ is the average velocity of the laminar flow of the carrier gas;
$\dot{m}_{cg}$ is the mass flow of the carrier gas;
$\rho_{cg}$ is the density of the carrier gas; and
$a$ is the radius of the processing chamber.

For example, average velocity of a laminar flow of a typical gas, nitrogen, at 100 sccm, 0.5 torr and 613K, is 10.4 cm/s.

The change rate of the concentration of the photoactive organic phase with time can be described by the convection-diffusion equation:

$$\frac{\partial c_p}{\partial t} = \vec{\nabla}\cdot(D_{org}\vec{\nabla}c_p) - \vec{\nabla}\cdot(\vec{u}_{cg}c_p) \quad (30)$$

where
$c_p$ is the concentration of the gas-phase photoactive organic material in the processing chamber;
$D_{org}$ is the diffusivity of the gas-phase photoactive organic material in the processing chamber; and
$u_{cg}$ is the velocity of the carrier gas in the processing chamber.

The diffusivity of the gas-phase photoactive organic material, $D_{org}$, can be obtained according to Champan-Enskog theory:

$$D_{AB} = D_0\frac{T^{3/2}}{P} = \frac{3k_B}{8\sigma_{AB}^2}\sqrt{\frac{k_B}{2\pi M_{AB}}}\frac{T^{3/2}}{P} \quad (31)$$

where
$D_{AB}$ is the diffusivity of organic component A into B, the component A being the gas-phase photoactive organic material and the component B being the carrier gas in the OVPD chamber;
T=the system temperature;
P=the system pressure;
$k_B$=Boltzmann constant;
$M_{AB}$=reduced mass of species A and B; and
$\sigma_{AB}$=0.5($\sigma_A+\sigma_B$), where $\sigma_A$ and $\sigma_B$ are the van der Waals interaction diameters of the organic components A and B respectively.

The reduced mass $M_{AB}$ expressed in number of molecules is given by:

$$M_{AB} = \frac{M_A \cdot M_B}{M_A + M_B} \quad (32)$$

Where $M_A$ and $M_B$ are the molar mass of the organic components A and B respectively. The value of $\sigma_A$ and $\sigma_B$ values are constants taken from literature and are well known. For example, the calculated diffusivity of Alq3 in nitrogen is $5.2 \times 10^{-5}$ m$^2$ K$^{1.5}$/s/Pa based on the following data: $\sigma_{Alq3}$ is 15 A, $M_{Alq3}$ is 0.459 Kg/mol.

Figure 12:
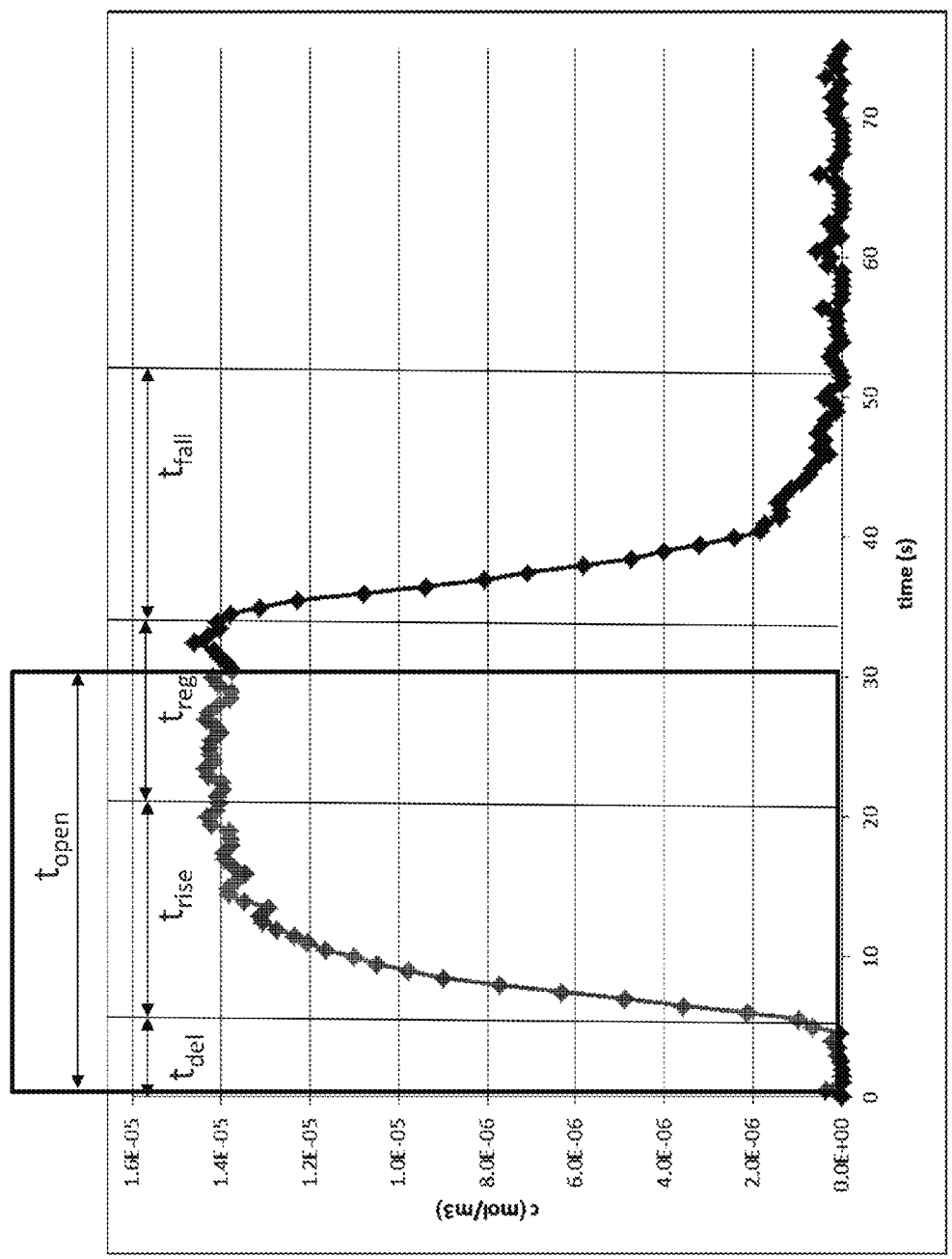
FIG. 12 illustrates a concentration level profile of a photoactive organic material measured in a non-steady dynamic state of depositing an organic film in a processing chamber, based on the method in accordance with some embodiments.

Considering these concepts, according to an embodiment, the PL emission monitoring method described herein can be used for monitoring a non-steady dynamic event inside an OPVD deposition processing chamber. FIG. 12 is an example of a concentration profile over time corresponding to a pulse of a gas-phase photoactive organic material being introduced into the deposition chamber. The gas-phase photoactive organic material was introduced into the OVPD processing chamber at time 0 s. The organic molecules were allow to mix with the inert carrier gas inside the processing chamber for a duration of 30 seconds ($t_{open}$) at flow rate of 50 sccm, after which the source for the photoactive organic molecules was closed. The organic species used in this example was Alq3 because it has high luminescent yield. The laser whose emission peak matched the absorption peak of Alq3 was chosen for irradiating Alq3 gas. This type of dynamic response is valid for any photoactive organic species that might be used in OVPD processing and thus the method and system of the present disclosure can be used to monitor the dynamic conditions of the photoactive organic species being deposited in the OVPD system.

During the experiment, the total flow rate $q_{tot}$ was 500 sccm, the total pressure $P_t$ was 1.5 torr. The chamber temperature ($T_t$) was 340° C. and the substrate temperature ($T_s$) was 290° C. Starting from time 0 s, the PL emission signal was monitored for a duration of 75 s. During the initial 5 seconds of delay time ($t_{del}$) the PL signal was insignificant because no organic molecules reached the chamber region traversed by the probing radiation (laser) beam. Between 5-20 seconds ($t_{rise}$), the concentration of organic gas increased abruptly. This phenomenon is described as a "burst" or a dynamic perturbation. Between about 20-30 second ($t_{reg}$) period after the time 0 s, the concentration of the photoactive organic molecules reached a steady state. The concentration level then decreased sharply during the period between 30-50 second ($t_{fall}$) period, corresponding to the closure of the source of the gas-phase organic molecules. The shape of the curve can be described by a combination of diffusive and convective physics. Using numerical calculation, one can simulate the mass transport of the gas-phase photoactive organic molecules cross the OVPD processing chamber.

Figure 13:
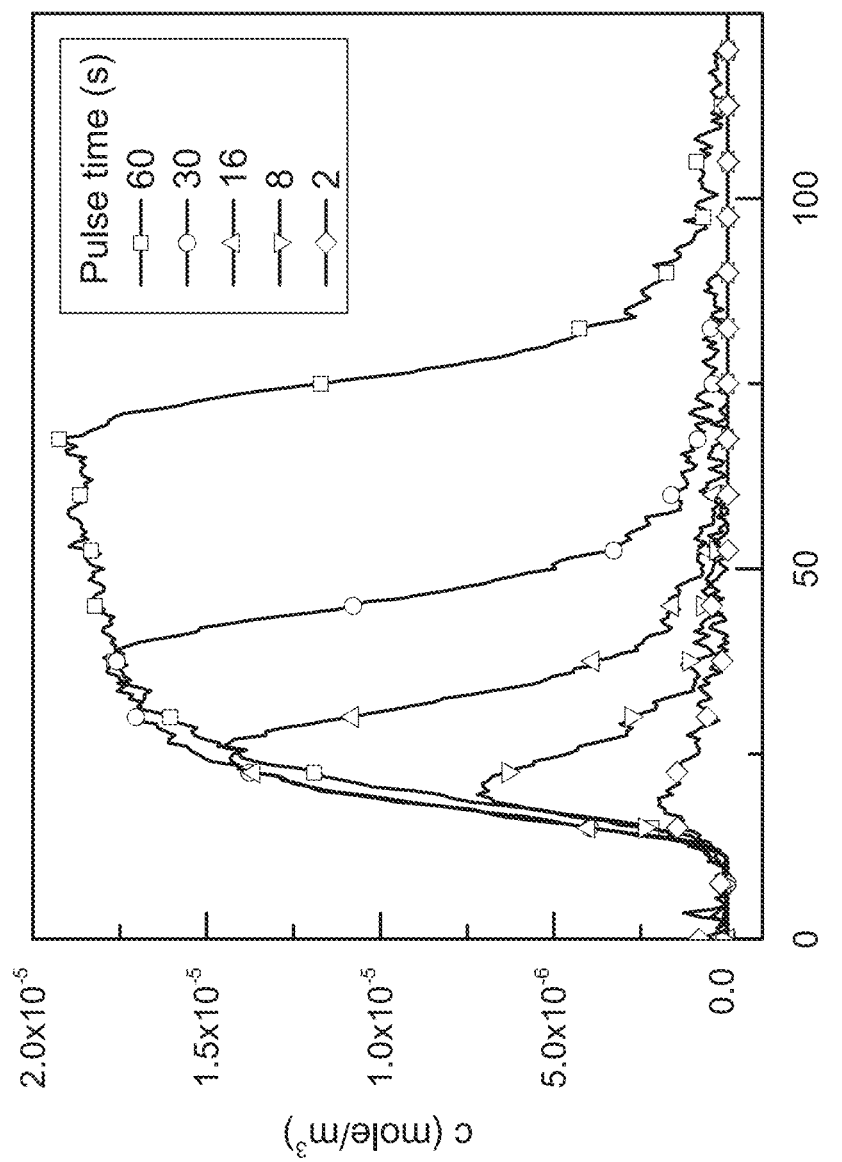
FIG. 13 illustrates the effect of source opening time on dynamic perturbation in concentration of a photoactive organic gas measured by the PL monitoring in situ and in real time while depositing an organic film.

FIG. 13 shows the effect of different organic molecule source opening duration times (i.e., pulse time or pulse width) on dynamic perturbation in concentration level of the photoactive organic material measured by the PL monitoring in situ and in real time while depositing an organic film. A suitable opening time can be selected to achieve stable deposition at a relatively steady state of supplying one or more organic gas.

Figure 14:
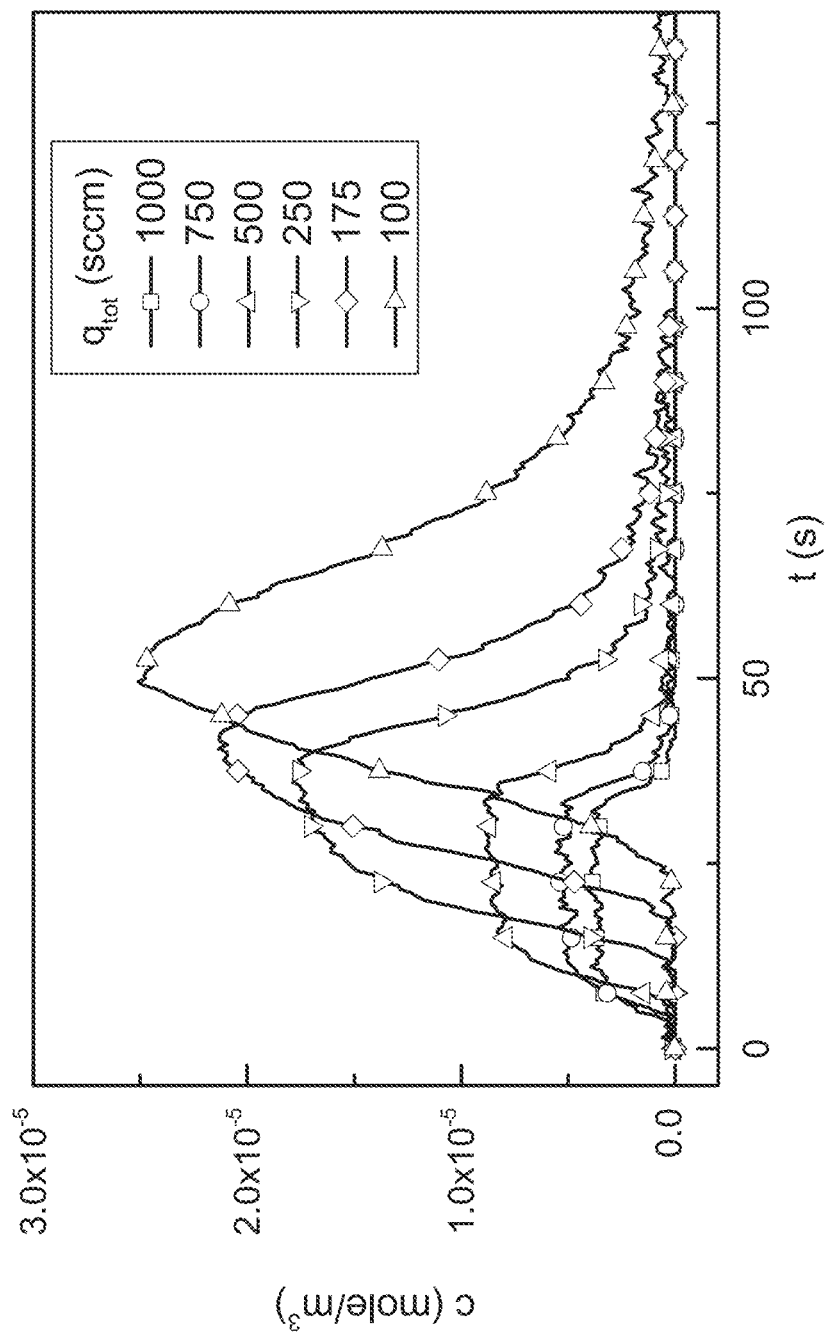
FIG. 14 illustrates effects of different carrier gas flow rates on dynamic concentration of a gas-phase photoactive organic material based on PL monitoring according to the present disclosure.

FIG. 14 shows effect of different carrier gas flow rates, $q_{tot}$, on dynamic concentration of the photoactive organic molecules measured by PL emission monitoring, in accordance with some embodiments. The duration of the pulse of the organic molecules was 30 seconds for all the experiments. Changes in the flow rate of the carrier gas significantly affect the concentration of the photoactive organic gas near the substrate for deposition.

Figure 15:
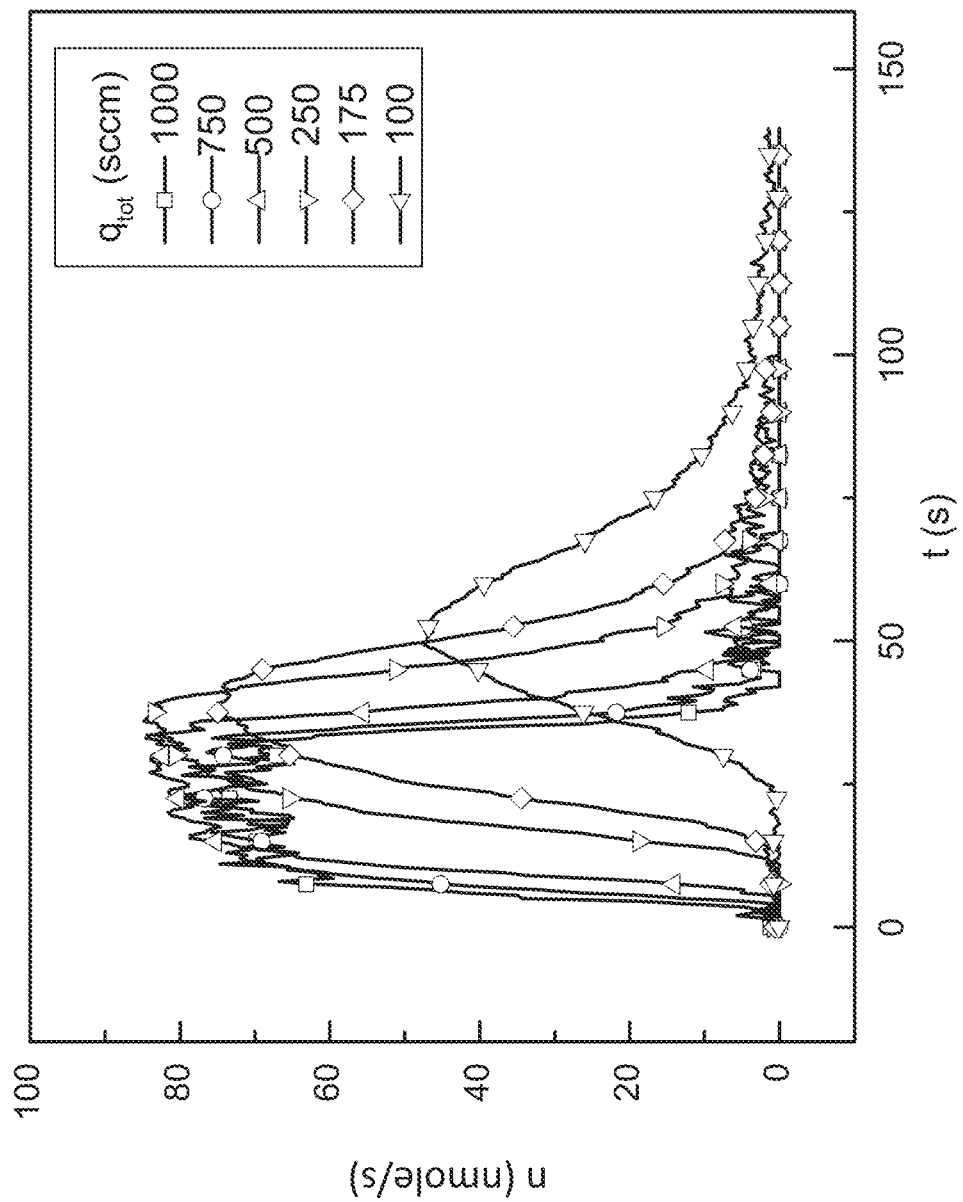
FIG. 15 illustrates exemplary profiles of a photoactive organic material transported in a dynamic perturbation under different flow rate, based on PL monitoring in accordance with some embodiments.
Figure 16:
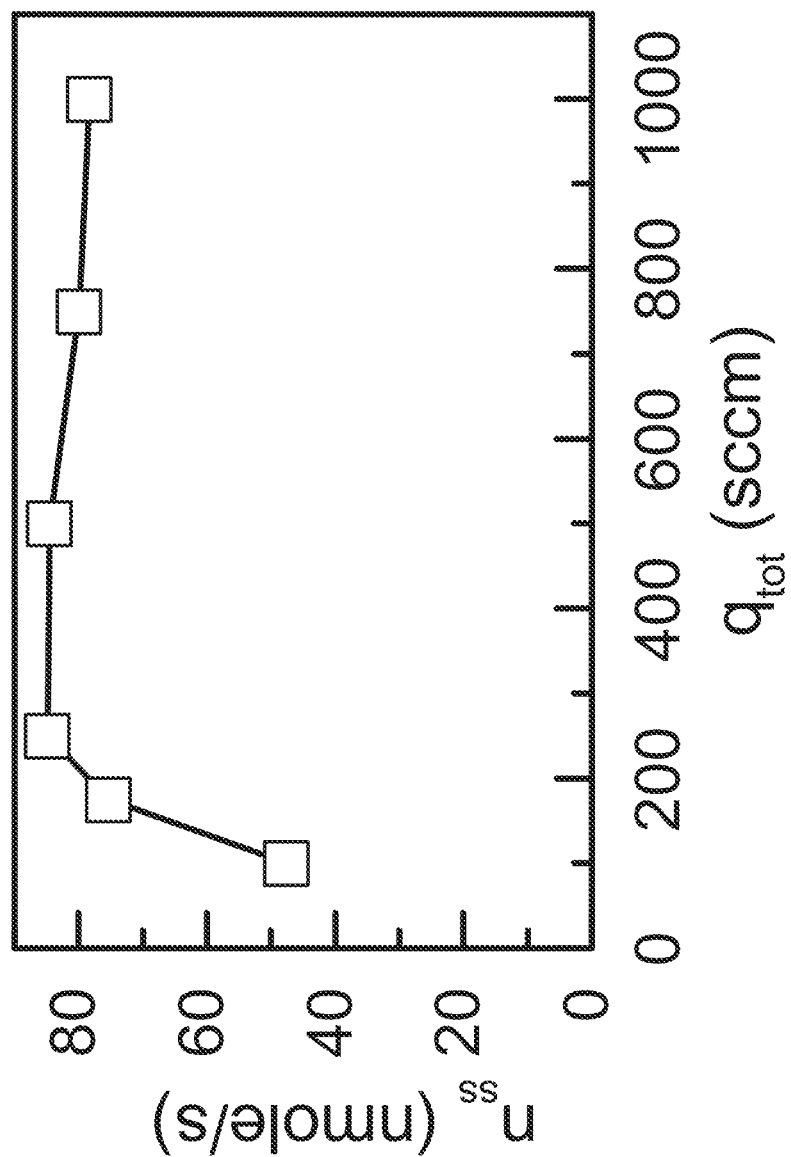
FIG. 16 illustrates the evolution of the steady-state molar flow rate of photoactive organic material ejected by the source as a function of carrier gas total mass flow rate. The molar flow rate are determined from height of profiles based on PL monitoring according to the present disclosure.

FIGS. 15-16 illustrate exemplary profile of a photoactive organic material transported in a dynamic perturbation under different flow rates, based on PL monitoring in accordance with some embodiments. FIG. 15 is equivalent to FIG. 14, except that the concentration levels are converted into molar flow rate of organic molecules by multiplying the concentration by the average velocity of the carrier gas, $u_{cg}$, and the cross-sectional area of the OVPD chamber $A_{ch}$, according to the following equation:

$$\dot{n}_{ch} = c_p \bar{u}_{cg} A_{ch} \quad (33)$$

where $\dot{n}_{ch}$ is the molar flow rate of the gas-phase photoactive organic material;

$\bar{u}_{cg}$ is the average velocity of the laminar flow of carrier gas; and $A_{ch}$ is the cross section area of the OVPD processing chamber.

The amount of the photoactive organic material transported in a dynamic perturbation is defined as follows:

$$n_{pulse} = \int_{t=0}^{\infty} \dot{n}_{ch} \, dt \quad (34)$$

where $n_{pulse}$ is the amount of the photoactive organic material transported in a dynamic perturbation.

FIG. 15 shows that the plateaus of the pulses fall onto each other. This means that once the system has reached a steady-state (i.e. plateau), the molar flow rate is the same. Indeed source operation (and thus source organic molar flow rate output) is only mildly affected by the total carrier gas flow $q_{tot}$ varied in this experiment. In other words, the amount of photoactive organic material transported in a dynamic perturbation is the same.

FIG. 16 shows the value of the steady state molar flow rate at different total carrier gas flow $q_{tot}$. They are equal except at lowest total flow rate ($q_{tot}$). This is because the pulse at the low total flow rate is not long enough to reach a steady state. Therefore, the PL monitoring described in the present disclosure is helpful to explore the operational properties of a given system as well as the photoactive molecules deployed in the system.

In some embodiments, the method comprises responding to a dynamic perturbation by making adjustment to providing the at least one photoactive organic gas in the processing chamber.

According to another embodiment, using a laser as the radiation source, a spatial concentration level distribution map of the one or more gas-phase photoactive organic materials inside the OVPD or VTE processing chamber 102, 400 can be generated. In order to generate such spatial distribution map, the interior space of the processing chamber 102, 400 is predefined into a plurality of zones or sections and each zone is then assigned with a location identifier that helps identify the location of that zone inside the processing chamber. Then, during the deposition process, one of the plurality of zones is irradiated with the light beam, thereby generating a PL emission from the gas-phase photoactive organic material in that zone. Preferably, the source of the irradiating light beam is of the kind and configured appropriately to be able to be focused and irradiate only the target zone. In one embodiment, a laser light beam is used in a manner described above in connection with other aspects of the present disclosure. Then, by detecting and measuring the intensity of the PL emission emanating from that zone, the concentration level of the gas-phase photoactive organic material in that zone can be determined using the calculations described above. The concentration level data is then paired with the location identifier for the corresponding zone. This process is then repeated for each of the predefined plurality of zones, thereby generating a set of paired data of the concentration level of the gas-phase photoactive organic material and the location identifiers for the corresponding zones. The set of paired data represents the spatial concentration level distribution map of the gas-phase photoactive organic material in the processing chamber 102, 400. The central processing unit 136 can be configured to store the spatial concentration level distribution map and output the map data in an appropriate format to the output device 139.

It should be noted that because the processing chamber 102, 400 is filled with the photoactive organic material, when a laser beam is used to irradiate an area inside the processing chamber, the organic molecules fluoresce along a line defined by the laser beam. By pointing and tuning the focus of the photodetector 134 to a specific point along that line of fluorescing organic molecules, one can choose to look at a small section of the line, the monitored region, in order to get a local reading of the concentration of the organic molecules in that monitored region. Thus, in the various embodiments of the method described herein, monitoring of a particular point or a region in the deposition processing chamber is achieved by the intersecting point of the irradiating laser beam and the photodector's focal point.

The size of the monitored region can be adjusted by controlling the diameter of the laser beam. Thus, by selecting smaller laser beam diameter, the spatial resolution can be increased. However, in both OVPD and VTE embodiments, as the monitored region is decreased, the number of the photoactive organic molecules in the monitored region also decreases, and the detectable PL signal is reduced, requiring more intense laser and more sensitive photodetector. In certain cases where the deposition process implements very low concentration of photoactive organic molecules in the processing chamber, the volume of the monitored region can be increased by using a larger diameter laser beam or a diverging light source and an out-of-focus photodetector. These adjustments would provide enough detectable PL signal at the expense of lower spatial resolution.

The method of the present disclosure can be applied to various gas-phase deposition systems, such as OVPD, VTE, CVD, etc. The method of the present disclosure can be applied to either fluorescent or phosphorescent photoactive organic molecules. The photoactive organic molecules can be any photoactive organic compound for use in organic electronics and optoelectronics. They generally comprise conjugated molecular structures with high molecular weight. For example, tris(8-hydroxyquinolinato) aluminum with the formula Al($c_9H_6NO$)$_3$, widely abbreviated Alq3, is a coordination complex wherein aluminum is bonded in a bidentate manner to the conjugate base of three 8-hydroxyquinoline ligands as shown in the formula below.

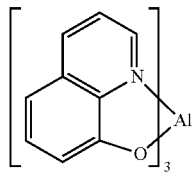

Other examples of photoactive molecules include Ir(mppy)$_3$,

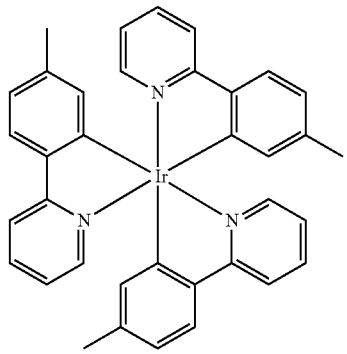

and phthalocyanine

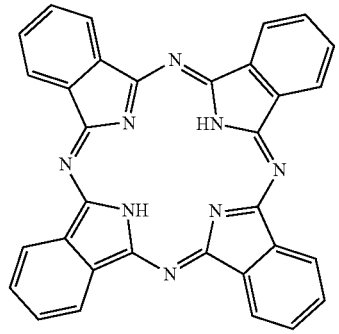 [SMILES: c1ccc2c(c1)-c1nc-2nc2[nH]c(nc3nc(nc4[nH]c(n1)c1ccccc41)-c1ccccc1-3)c1ccccc21]

Additional examples of photoactive organic materials to which the method of the present disclosure can be applied can be found from the following non-exhaustive list of materials:
<<Organic Materials Suitable as Red Dopants in OLEDs:>>
DCM: (E)-2-(2-(4-(dimethylamino)styryl)-6-methyl-4H-pyran-4-ylidene)malononitrile; DCM2: 4-(dicyanomethylene)-2-methyl-6-julolidyl-9-enyl-4H-pyran; Eu(dbm)3(Phen): Tris(dibenzoylmethane)phenanthroline europium(III); Rubrene: 5,6,11,12-tetraphenylnaphthacene; Ir(btp)2(acac): Bis(2-benzo[b]thiophen-2-yl-pyridine)(acetylacetonate)iridium(III); Ir(piq)3: Tris(1-phenylisoquinoline)iridium(III); Ru(dtb-bpy)3.2(PF6): Tris[4,4'-di-tert-butyl-(2,2)-bipyridine]ruthenium(III) complex; Ir(2-phq)2(acac): Bis(2-phenylquinoline)(acetylacetonate)iridium(III); Pt(TPBP): 5,10,15,20-tetraphenyltetrabenzoporphyrin platinum complex; Os(fppz)2(PPhMe2)2; Osmium(II) bis(3-trifluoromethyl-5-(2-pyridyl)-pyrazolate) dimethylphenylphosphine; Ir(Mphq)3: Tris[2-phenyl-4-methylquinoline)]iridium(III); fac-Ir(ppy)2Pc: Bis(2-phenylpyridine)(3-(pyridin-2-yl)-2H-chromen-2-onate)iridium(III); PtOEP: Pt(II) octaethylporphine.
<<Organic Materials Suitable as Fluorescent Hosts in OLEDs:>>
Alq3: Tris(8-hydroxy-quinolinato)aluminium; AND: 9,10-di(naphth-2-yl)anthracene; TBADN: 2-tert-butyl-9,10-di(naphth-2-yl)anthracene; TDAF: 2,7-bis[9,9-di(4-methylphenyl)-fluoren-2-yl]-9,9-di(4-methylphenyl)fluorene; MADN: 2-methyl-9,10-bis(naphthalen-2-yl)anthracene; BSBF: 2-(9,9-spirobifluoren-2-yl)-9,9-spirobifluorene; TSBF: 2,7-bis(9,9-spirobifluoren-2-yl)-9,9-spirobifluorene; BDAF: 2-[9,9-di(4-methylphenyl)-fluoren-2-yl]-9,9-di(4-methylphenyl)fluorene; 2,2'-Spiro-Pye: 2,2'-dipyrenyl-9,9-spirobifluorene; TPB3:1,3,5-tri(pyren-1-yl)benzene; BPPF: 9,9-bis[4-(pyrenyl)phenyl]-9H-fluorene; TPBA: 2,2'-bi(9, 10-diphenyl-anthracene); Spiro-Pye: 2,7-dipyrenyl-9,9-spirobifluorene; p-Bpye: 1,4-di(pyren-1-yl)benzene; m-Bpye: 1,3-di(pyren-1-yl)benzene; DBPenta: 6,13-di-biphenyl-4-yl-pentacene; DNP: 3,9-di(naphthalen-2-yl)perylene and 3,10-di(naphthalen-2-yl)perylene mixture; TPyPA: Tris[4-(pyrenyl)-phenyl]amine; BANE: 10,10'-di(biphenyl-4-yl)-9,9'-bianthracene; 4P—NPB: N,N'-di-(1-naphthalenyl)-N,N'-diphenyl-[1,1':4',1":4'",1'''-quaterphenyl]-4,4'''-diamine; BUBH-3: 4,4'-di[10-(naphthalen-1-yl)anthracen-9-yl]biphenyl; DBP: Dibenzo{[f,f]-4,4',7,7'-tetraphenyl}diindeno[1,2,3-cd:1',2',3'-lm]perylene; BAnFPye:1-(7-(9,9'-bianthracen-10-yl)-9,9-dimethyl-9H-fluoren-2-yl)pyrene; DAnF6Pye: 1-(7-(9,9'-bianthracen-10-yl)-9,9-dihexyl-9H-fluoren-2-yl)pyrene.

<<Organic Materials Suitable as Green Dopants in OLEDs:>>
Coumarin 6: 3-(2-benzothiazolyl)-7-(diethylamino)coumarin; DMQA: N,N'-dimethyl-quinacridone; Ir(ppy)3: Tris(2-phenylpyridine)iridium(III); Ir(ppy)2(acac): Bis(2-phenylpyridine)(acetylacetonate)iridium(III); TTPA: 9,10-bis[N,N-di-(p-tolyl)-amino]anthracene; TPA: 9,10-bis[phenyl(m-tolyl)-amino]anthracene; Zn(BTZ)2: Bis[2-(2hydroxyphenyl)benzothiazolato]zinc(II); BA-TAD: N10,N10,N10',N10'-tetraphenyl-9,9'-bianthracene-10,10'-diamine; Ir(ppy)2(m-bppy): Bis(2-phenylpyridinato)[2-(biphenyl-4-yl)pyridinato]Iridium(III).

<<Organic Materials Suitable as Blue Dopants in OLEDs:>>
BCzVBi: 4,4'-bis(9-ethyl-3-carbazovinylene)-1,1'-biphenyl; TBPe: 2,5,8,11-tetra-tert-butylperylene; BCzVB: 1,4-bis[2-(3-N-ethylcarbazoryl)vinyl]benzene; DPAVBi: 4,4'-bis[4-(di-p-tolylamino)styryl]biphenyl; FIrPic: Bis(3,5-difluoro-2-(2-pyridyl)phenyl-(2-carboxypyridyl)iridium(III); FIr6: Bis(2,4-difluorophenylpyridinato)tetrakis(1-pyrazolyl)borate iridium(III); BNP3FL: N,N'-bis(naphthalen-2-yl)-N,N'-bis(phenyl)-tris-(9,9-dimethylfluorenylene); DBzA: 6-methyl-2-(4-(9-(4-(6-methylbenzo[d]thiazol-2-yl)phenyl)anthracen-10-yl)phenyl)benzo[d]thiazole; FIrN4: Bis(2,4-difluorophenylpyridinato)(5-(pyridin-2-yl)-1H-tetrazolate)iridium(III); BTP: 2,2'-bitriphenylene; TPIP: 4,4'-bis(1-p-tolyl-1H-phenanthro[9,10-d]imidazol-2-yl)biphenyl.

<<Photoactive Organic Materials Suitable for Organic Photovoltaic Applications and Appropriate for Implementing the Method of the Present Invention>>
Choloro[subphthalocyaninato]boron (III) (aka SubPc); 3,4,9,10-perylene-tetracarboxylic bis-benzimidazole (aka PTCBI); c$_{70}$, and the family of Squaraines (which has a low but measurable PL).

Those skilled in the art may appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the attached claims.

The data of the at least one processing parameter measured in steady state or a dynamic state are useful to control the deposition process for an organic film with good quality.

Emission spectrum is the distribution of electromagnetic radiation released by a substance whose atoms have been excited by heat or radiation. Absorption profile of a given organic material is the range of electromagnetic radiation wavelengths that are absorbed by the organic material resulting in emission of the characteristic radiation having the emission spectrum.

What is claimed is:

1. A method of monitoring organic materials in-situ during a deposition process for depositing a film of one or more photoactive organic materials from one or more gas-phase photoactive organic materials onto a substrate in a processing chamber, the method comprising:

(a) irradiating at least one of the one or more gas-phase photoactive organic materials at a monitored region inside the processing chamber with a radiation beam in-situ during the deposition process, thereby generating a photoluminescence emission having an intensity from the at least one of the one or more gas-phase photoactive organic materials being irradiated;

(b) measuring the intensity $P_{PL}$ of the photoluminescence emission from the at least one of the one or more gas-phase photoactive organic materials being irradiated;

(c) for each gas-phase photoactive organic material being irradiated, determining from the intensity of the photoluminescence emission, at least one processing parameter associated with depositing the gas-phase photoactive organic material, wherein the at least one processing parameter is a concentration level $c_p$ of the gas-phase photoactive organic material; and (d) calibrating the deposition process before step (a) by calculating a concentration conversion factor $k_c$ for each gas-phase photoactive organic material being irradiated, wherein the calibrating step comprises:

(e) depositing a sacrificial calibration film of the gas-phase photoactive organic material on a sacrificial calibration substrate for a fixed time duration using known process conditions, wherein the gas-phase photoactive organic material has a calibration concentration level $c_{p,exp}$ in the processing chamber;

(f) irradiating the gas-phase photoactive organic material in the monitored region during step (e), resulting in a photoluminescence emission and measuring the intensity $P_{PL,exp}$ of the photoluminescence emission;

(g) measuring the sacrificial calibration film's thickness;

(h) calculating deposition rate $r_{dep,exp}$ of the calibration film by dividing the calibration film's thickness by the fixed time duration;

(i) where the deposition process is a VTE process and the processing chamber is a VTE deposition chamber provided with an evaporation source crucible for producing the gas-phase or organic photoactive material, calculating the calibration concentration level $c_{p,exp}$ of the gas-phase photoactive organic material by using equation (21) below, $$C_{p,exp} = \frac{r_{0,p}^2 r_s^A}{r_p^A r_{0,s}^2} \cdot \frac{\rho_{org}}{\bar{v}} \cdot r_{dep,exp} \quad (21)$$

where $r_{0,p}$ is the distance from the evaporation source crucible to the monitored region, $r_p$ is the distance from the evaporation source crucible to the monitored region, $r_s$ is the distance from the evaporation source crucible to the center of the substrate, $r_{0,s}$ is the distance from the evaporation source crucible to the surface of the substrate along the diffusion axis, $\rho_{org}$ is molar density of the deposited organic material, or where the deposition process is an OVPD process and the processing chamber is an OVPD deposition chamber, calculating the calibration concentration level $c_{p,exp}$ by using equation (23) below, $$C_{p,exp} = \frac{\delta_{BL}}{D_{org}} J_{dep} = \frac{\delta_{BL}\rho_{org}}{D_{org}} r_{dep,exp} \qquad (23)$$

where $J_{dep}$ is the organic species flux onto the substrate;

$\delta_{BL}$ is the boundary layer thickness, the boundary layer being formed by the carrier gas on top of the substrate through which the organic molecules must diffuse in order to condense on the substrate and form a film of a certain thickness;

$D_{org}$ is diffusivity of organic molecules in the carrier gas;

$\rho_{org}$ is the molar density of the deposited organic material; and $r_{dep}$ is the film deposition rate onto the substrate; and (j) calculating the concentration level conversion factor $k_c$ by using the following equation (15):

$$k_c = \frac{c_{p,exp}}{P_{PL,exp} - P_{PL,baseline}} \qquad (15)$$

where $P_{PL,baseline}$ is the average baseline intensity in the processing chamber detected by the photodetector before any photoactive organic materials for the deposition process is introduced into the processing chamber.

2. The method of claim 1, wherein the step (c) is performed in real time while depositing the film.

3. The method of claim 1, wherein the concentration level $c_p$ of the gas-phase photoactive organic material at the monitored region is determined from the measured intensity $P_{PL}$ of the photoluminescence emission by using the following equation (13):

$$c_p = k_c(P_{PL} - P_{PL,baseline}) \qquad (13).$$

4. The method of claim 1, wherein each of the one or more gas-phase photoactive organic materials has a photo-absorption profile and the radiation beam is generated by a radiation source that is configured to emit a radiation having an emission spectrum that matches the photo-absorption profile of the at least one gas-phase photoactive organic material being irradiated.

5. The method of claim 1, wherein the intensity of the photoluminescence emission from each of the gas-phase photoactive organic material being irradiated is measured using a photodetector.

6. The method of claim 1, wherein the intensity of the photoluminescence emission from each of the gas-phase photoactive organic material being irradiated is measured using a corresponding number of photodetectors for each of the at least one gas-phase photoactive organic material being irradiated.

7. The method of claim 6, wherein the photoluminescence emission from each of the gas-phase photoactive organic material being irradiated is at a different wavelength and each of the photodetectors is configured for measuring the intensity of the photoluminescence emission from the respective organic material.

8. The method of claim 1, wherein each of the gas-phase photoactive organic materials being irradiated having a characteristic photoluminescence emission spectrum and the intensity of the photoluminescence emission from the gas-phase photoactive organic materials being irradiated is spectrally resolved by measuring it with a spectrometer, further wherein a contribution from each of the gas-phase photoactive organic material being irradiated is isolated according to the characteristic photoluminescence emission spectrum.

9. The method of claim 1, wherein determining the at least one processing parameter is performed by a microprocessor operably connected with the photodetectors.

10. The method of claim 9, further comprising the microprocessor outputting the at least one processing parameter to an output device.

* * * * *